US011661593B2

(12) United States Patent
Hasslacher et al.

(10) Patent No.: US 11,661,593 B2
(45) Date of Patent: *May 30, 2023

(54) METHODS OF PURIFYING RECOMBINANT ADAMTS13 AND OTHER PROTEINS AND COMPOSITIONS THEREOF

(71) Applicant: TAKEDA PHARMACEUTICAL COMPANY LIMITED, Osaka (JP)

(72) Inventors: Meinhard Hasslacher, Vienna (AT); Christian Fiedler, Vienna (AT); Christa Mayer, Wolfsthal (AT); Artur Mitterer, Orth/Donau (AT)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/571,670

(22) Filed: Dec. 16, 2014

(65) Prior Publication Data
US 2015/0104849 A1 Apr. 16, 2015

Related U.S. Application Data

(63) Continuation of application No. 12/847,956, filed on Jul. 30, 2010, now Pat. No. 8,945,895.

(60) Provisional application No. 61/230,308, filed on Jul. 31, 2009.

(51) Int. Cl.
C12N 9/64 (2006.01)
C12N 11/14 (2006.01)
C12M 1/00 (2006.01)

(52) U.S. Cl.
CPC .......... *C12N 9/6489* (2013.01); *C12M 47/12* (2013.01); *C12N 11/14* (2013.01); *C12Y 304/24087* (2013.01)

(58) Field of Classification Search
CPC ................ C12N 9/6489; C12M 47/12; C12Y 304/24087
See application file for complete search history.

(56) References Cited

U.S. PATENT DOCUMENTS

| 4,239,854 | A | * | 12/1980 | Hirahara | B01J 43/00 435/180 |
| 4,540,573 | A | * | 9/1985 | Neurath | A61L 2/0023 424/529 |
| 5,283,182 | A | * | 2/1994 | Powell | C12N 11/082 435/106 |
| 5,296,228 | A | * | 3/1994 | Chang | A61K 9/0048 424/422 |
| 5,371,195 | A | | 12/1994 | Grandgeorge et al. | |
| 5,470,954 | A | * | 11/1995 | Neslund | C07K 14/755 435/325 |
| 5,578,480 | A | * | 11/1996 | Khandke | C12N 9/88 435/232 |
| 5,716,645 | A | * | 2/1998 | Tse | A61L 24/043 424/530 |
| 5,786,458 | A | | 7/1998 | Baumbach et al. | |
| 5,907,032 | A | * | 5/1999 | MacGregor | C12Y 304/21005 424/529 |
| 6,251,860 | B1 | | 6/2001 | Parkkinen et al. | |
| 6,429,192 | B1 | | 8/2002 | Laursen | |
| 6,468,733 | B2 | | 10/2002 | Nur | |
| 7,037,658 | B2 | | 5/2006 | Ginsburg et al. | |
| 7,270,976 | B2 | | 9/2007 | Greenfield | |
| 2001/0034053 | A1 | * | 10/2001 | Winge | C07K 14/47 435/212 |
| 2002/0170859 | A1 | | 11/2002 | Kopf | |
| 2003/0133829 | A1 | * | 7/2003 | Anderle | A61L 2/0088 422/28 |
| 2003/0190318 | A1 | * | 10/2003 | Torigoe | C07K 16/2866 424/143.1 |
| 2005/0239167 | A1 | * | 10/2005 | Fleer | C07K 14/575 435/325 |
| 2005/0282250 | A1 | * | 12/2005 | Hertenberger | C12N 9/1205 435/69.1 |
| 2006/0073535 | A1 | * | 4/2006 | Greenfield | C12Q 1/37 435/7.92 |
| 2006/0110407 | A1 | * | 5/2006 | Stopera | A61K 39/42 424/232.1 |
| 2006/0134769 | A1 | * | 6/2006 | Connolly | A61L 2/0088 435/214 |
| 2006/0193966 | A1 | * | 8/2006 | Wu | A23J 3/16 426/656 |
| 2006/0233784 | A1 | | 10/2006 | Ginsburg et al. | |

(Continued)

FOREIGN PATENT DOCUMENTS

EP 0286323 10/1988
EP 0785213 7/1997

(Continued)

OTHER PUBLICATIONS

Johnston et al. The Use of Chromatography to Manufacture Purer and Safer Plasma Products., Biotechnology and Genetic Engineering Reviews (2000), vol. 17, pp. 37-70.*

(Continued)

*Primary Examiner* — Anand U Desai
(74) *Attorney, Agent, or Firm* — Troutman Pepper Hamilton Sanders LLP

(57) ABSTRACT

Provided herein are methods for purifying recombinant A Disintegrin-like and Metallopeptidase with Thrombospondin Type 1 Motif 13 (ADAMTS13) protein from a sample. The method comprises enriching for ADAMTS13 protein by chromatographically contacting the sample with hydroxyapatite under conditions that allow ADAMTS13 protein to appear in the eluate or supernatant from the hydroxylapatite. The methods may further comprise tandem chromatography with a mixed mode cation exchange/hydrophobic interaction resin that binds ADAMTS13 protein. Additional optional steps involve ultrafiltration/diafiltration, anion exchange chromatography, cation exchange chromatography, and viral inactivation. Also provided herein are methods for inactivating virus contaminants in protein samples, where the protein is immobilized on a support. Also provided herein are compositions of ADAMTS13 prepared according to said methods.

11 Claims, 2 Drawing Sheets

(56) References Cited

U.S. PATENT DOCUMENTS

| | | | |
|---|---|---|---|
| 2006/0246589 A1 | 11/2006 | Ginsburg et al. | |
| 2007/0015703 A1 | 1/2007 | Wagner | |
| 2007/0065895 A1 | 3/2007 | Miyata et al. | |
| 2007/0299250 A1 | 12/2007 | Kretschmar et al. | |
| 2008/0020416 A1* | 1/2008 | McAlister | C12N 9/6462 435/23 |
| 2008/0207878 A1 | 8/2008 | Michel et al. | |
| 2009/0130714 A1* | 5/2009 | Majumder | C12N 9/6459 435/69.1 |
| 2009/0215025 A1* | 8/2009 | Knor | C07K 5/1016 435/4 |
| 2009/0215699 A1* | 8/2009 | Bacher | A61K 38/08 514/10.3 |
| 2010/0193440 A1* | 8/2010 | Bridey | C12N 9/6489 210/656 |
| 2011/0097318 A1* | 4/2011 | Gadgil | A61M 5/2448 141/2 |

FOREIGN PATENT DOCUMENTS

| | | |
|---|---|---|
| EP | 0815873 | 1/1998 |
| EP | 0816377 | 1/1998 |
| EP | 1161958 | 12/2001 |
| EP | 1958626 | 8/2008 |
| EP | 1990421 | 11/2008 |
| EP | 2172544 | 4/2010 |
| JP | 2003512594 | 4/2003 |
| JP | 2005-538686 | 12/2005 |
| JP | 2007-174977 | 7/2007 |
| WO | 199317724 | 9/1993 |
| WO | 1993022337 | 11/1993 |
| WO | 200001407 | 1/2000 |
| WO | 200242441 | 5/2002 |
| WO | WO 03/016492 | 2/2003 |
| WO | WO 03/053477 | 7/2003 |
| WO | 2004007533 | 1/2004 |
| WO | WO 2005/099858 | 4/2005 |
| WO | 2005121163 | 12/2005 |
| WO | WO 2008/057074 | 5/2008 |
| WO | 2009007451 | 1/2009 |

OTHER PUBLICATIONS

Scott et al. Comparison and stability of ADAMTS13 activity in therapeutic plasma products., Transfusion (2007), vol. 47, Issue 1, pp. 120-125.*

Lapecorella et al. Factor VII deficiency: defining the clinical picture and optimizing therapeutic options., Haemophilia (2008), vol. 14, pp. 1170-1175.*

Meyer-Siegler et al. Inhibition of macrophage migration inhibitory factor decreases proliferation and cytokine expression in bladder cancer cells., BMC Cancer (2004), vol. 4:64, pp. 120-125.*

Aranha et al. Viral Clearance Strategies for Biopharmaceutical Safety., Pharmaceutical Technology (2001), pp. 26-31.*

Gagnon (1998), Inactivating Virus Without Inactivating Your Product., Autumn 1998 issue of Validate Biosystmes Quarterly Resource Guide to Downstream Processing.*

Alexandratos SD (2008) Ion-Exchange Resins: A Retrospective from Industrial and Engineering Chemistry Research, Ind. Eng. Chem. Res., vol. 48, pp. 388-398.*

Norouzian D. (2003) Enzyme immobilization: the state of art in biotechnology, Iranian J. Biotechnol., vol. 1, No. 4, pp. 197-206).*

Fisher J. ("Genengnews" [GEN] (2008) vol. 28, No. 17, pp. 1-6.*

Horowitz et al., "Inactivation of Viruses in Labile Blood Derivatives. I. Disruption of Lipid-Enveloped Viruses by Tri(n-butyl)phosphate Detergent Combinations," Transfusion, vol. 25, No. 6, pp. 516-522, 1985.

Baxter Healthcare S.A. et al., Search Results issued by the Eurasian Patent Office for Eurasian Patent Application No. 201500952, Feb. 8, 2016, 2 pages.

Antoine et al., "ADAMTS13 Gene Defects in Two Brothers with Constitutional Thrombotic Thrombocytopenic Purpura and Normalization of von Willebrand Factor-Cleaving Protease Activity by Recombinant Human ADAMTS13," British Journal of Haematology, vol. 120, No. 5, pp. 821-824, Mar. 1, 2003.

Baudier et al., "Characterization of the Tumor Suppressor Protein p54 as a Protein Kinase C Substrate and a S100b-binding Protein," Proc. Natl. Acad. Sci., vol. 89, pp. 11627-11631, 1992.

Crawley et al., "Proteolytic Inactivation of ADAMTS13 by Thrombin and Plasmin," Blood, vol. 105, pp. 1085-1093, 2005.

Fujikawa et al., "Purification of Human von Willebrand Factor-Cleaving Protease and its Identification as a New Member of the Metailoproteinase Family," Blood, vol. 98, pp. 1662-1666, 2001.

Gardner et al., "A Functional Calcium-Binding Site in the Metalloprotease Domain of ADAMTS13," Blood, vol. 113, pp. 1149-1157, 2008.

Gerritsen et al., "Partial Amino Acid Sequence of Purified von Willebrand Factor-Cleaving Protease," Blood, vol. 98, pp. 1654-1661, 2001.

Kim et al., "Solvent/Detergent Inactivation and Chromatographic Removal of Human Immunodeficiency Virus During the Manufacturing of a High Purity Antihemophilic Factor VIII Concentrate," The Journal of Microbiology, vol. 38, pp. 187-191, 2000.

Levy et al., "ADAMTS13 Turns 3," Blood, vol. 106, pp. 11-17, 2005.

Low et al., "Future of Antibody Purification," Journal of Chromatography, vol. 848, pp. 48-63, 2007.

Plaimauer et al., "Expression and Characterization of Recombinant Human ADAMTS-13," Seminars in Hematology, vol. 41, No. 1, pp. 24-33, Jan. 2004.

Rosendahl, et al., "Identification and Characterization of a Pro-tumor Necrosis Factor-α-processing Enzyme from the ADAM Family of Zinc Metalloproteases," J. Biol. Chem., 272(39), pp. 24588-24593, 1997.

Rosengren et al., "Plasma Protein Absorption Pattern on Characterized Ceramic Biomaterials," Biomaterials, vol. 23, pp. 1237-1247, 2002.

Westling, et al., "ADAMTS4 Cleaves at the Aggrecanase Site (Glu373-Ala374) and Secondarily at the Matrix Metalloproteinase Site (Asn341-Phe342) in the Aggrecan Interglobular Domain," J. Biol. Chem., 277, pp. 16059-16066, 2002.

WHO Technical Report, 2004.

Zheng et al., "Structure of von Willebrand Factor-Cleaving Protease (ADAMTS13), a Metalloprotease Involved in Thrombotic Thrombocytopenic Purpura," The Journal of Biological Chemistry, vol. 276, pp. 41059-41063, 2001.

Baxter Healthcare, S.A. et al., Written Opinion and Search Report for Singapore Patent Appln. No. 201200658.1 dated Apr. 15, 2013, 17 pages.

Baxter Healthcare, S.A. et al., Written Opinion for Singapore Patent Appln. No. 201200658.1 dated Jan. 16, 2014, 11 pages.

Baxter International, Inc. et al., Patent Examination Report for Australian Patent Application No. 2010277491, dated Jun. 10, 2014, 4 pages.

Baxter International, Inc. et al., Notice of Reasons for Rejection for Japanese Patent Application No. 2012-522191, dated Nov. 25, 2014, 5 pages.

Edwards et al., "Tri(ii-butyl) phosphate/detergent treatment of licensed therapeutic and experimental blood derivatives", VOX SANG, (1987), vol. 52, pp. 53-59, XP000571683.

IP.com Prior Art Database Technical Disclosure [retrieved from the internet on Mar. 6, 2017] <URL:file:///C:/Users/cpaknu/Downloads/IPCOM000183319D%20(2).pdf> published May 18, 2009.

Boschetti N. and Johnston A., 'Virus Elimination and Validation,' Methods in Molecular Biology—Therapeutic Proteins: Methods and Protocols. (2005), vol. 308, pp. 209-219.

Gagnon P., Inactivating Virus Without Inactivating Your Product, Validated Biosystems Quarterly Resource Guide to Downstream Processing. (1998), (onlie journal) [retrieved from the internet on Mar. 7, 2017 <URL: http://www.validated.com/revalbio/pdffiles/virex.pdf>.

Jul. 18, 2017 European Search Report issued in connection with EP 17155619.

(56) References Cited

OTHER PUBLICATIONS

"Separations Technology" Ed. Wayne P. Olsen, pp. 369-383 (1995).
"Laboratory Techniques in Chemistry and Biochemistry" Eds. P.S. Diamond and R.F. Denman, pp. 271-274 (1973).
Office Action dated Dec. 21, 2022 in connection with Eurasian Application No. 201992487.
P. Roberts, Resistance of vaccinia virus to inactivation by solvent/detergent treatment of blood products. Biologicals. Mar. 2000:28(1):29-32. doi: 10.1006/biol.1999.0236.
Peter L. Roberts. Virus inactivation in a factor VIII/VWF concentrate treated using a solvent/detergent procedure based on polysorbate 20. Biologicals. Jan. 2009;37(1):26-31. doi: 10.1016/j.biologicals. 2008.08.003. Epub Oct. 10, 2008.
Peter L. Roberts. Virus inactivation by solvent/detergent treatment using Triton X-100 in a high purity factor VIII. Biologicals. Sep. 2008 36(5):330-5. doi: 10.1016/j.biologicals.2008.06.002.

\* cited by examiner

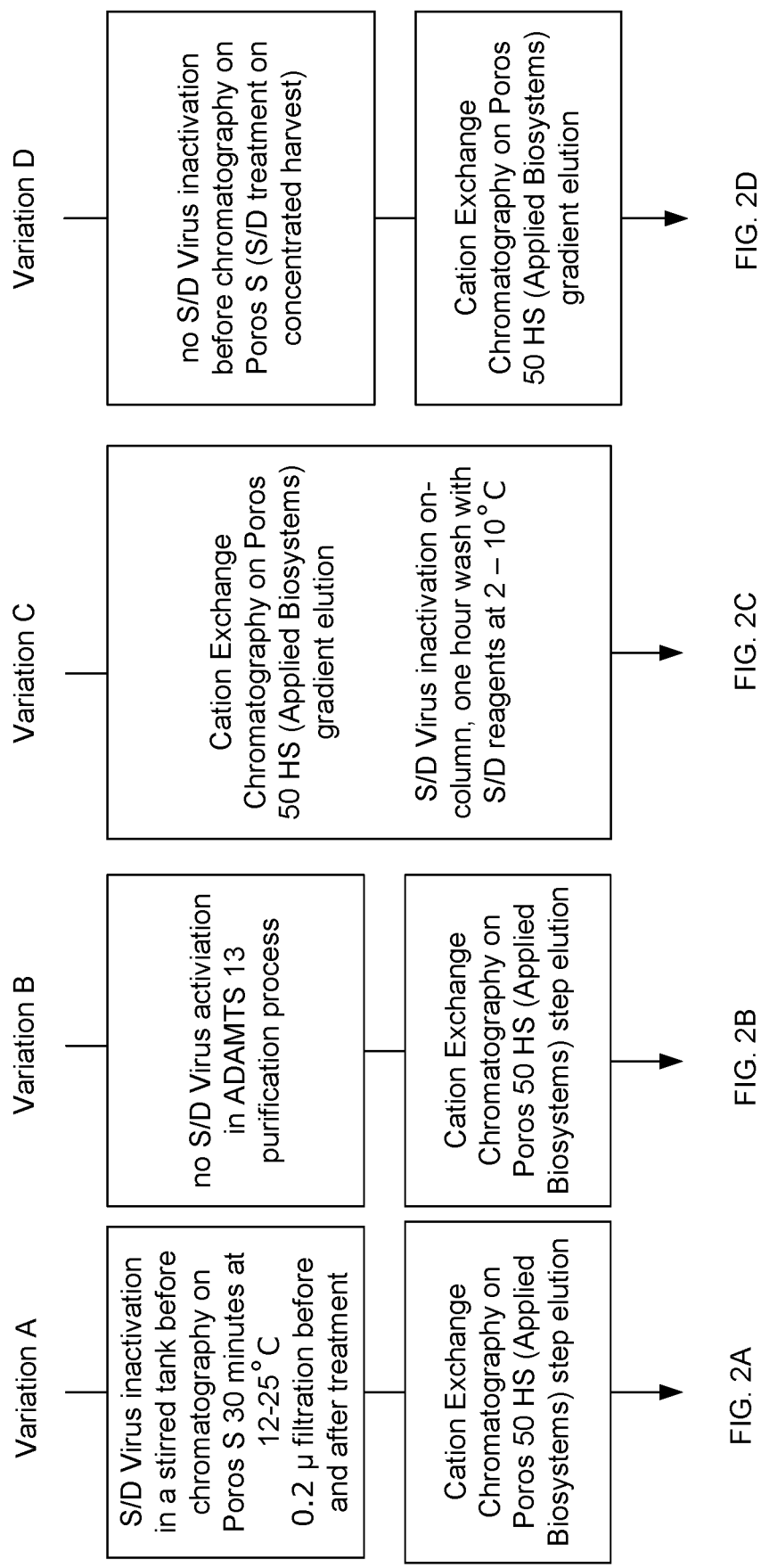

METHODS OF PURIFYING RECOMBINANT ADAMTS13 AND OTHER PROTEINS AND COMPOSITIONS THEREOF

CROSS REFERENCE TO RELATED APPLICATIONS

This application claims benefit of U.S. application Ser. No. 12/847,956 filed on Jul. 30, 2010, now U.S. Pat. No. 8,945,895, which claims benefit of U.S. Provisional Application No. 61/230,308, filed Jul. 31, 2009, each of which is hereby incorporated by reference in its entirety, and to which applications we claim priority.

FIELD OF INVENTION

The present invention relates generally to methods of purifying recombinant A Disintegrin-Like And Metallopeptidase with ThromboSpondin Type 1 Motif 13 (ADAMTS13) and other proteins, and compositions comprising such purified proteins.

BACKGROUND OF THE INVENTION

The metalloproteinase gene family, ADAM (a disintegrin and metalloproteinase), includes members that are membrane-anchored proteases with diverse functions. ADAMTS family members are distinguished from ADAMs by the presence of one or more thrombospondin 1-like (TSP1) domain(s) at the C-terminus and the absence of the EGF repeat, transmembrane domain and cytoplasmic tail typically observed in ADAM metalloproteinases.

A Disintegrin-Like and Metallopeptidase with Thrombospondin Type 1 Motif 13 (ADAMTS13) is a member of the ADAMTS family. ADAMTS13 has eight thrombospondin domains and no hydrophobic transmembrane domain. Accordingly, it is secreted. ADAMTS13 cleaves von Willebrand Factor at the $Tyr^{1605}$-$Met^{1606}$ bond and requires both calcium and zinc ions to function. ADAMTS13 is also known as "von Willebrand Factor-Cleaving Protease" and "VWFCP."

Deficient ADAMTS13 expression has been implicated in the pathogenesis of some diseases, e.g., thrombotic disorders such as thrombotic thrombocytopenic purpura (TTP) (see, e.g., U.S. Patent Publication No. 20070015703). In TTP, deficiency and/or inhibition of ADAMTS13 results in extensive microscopic thomboses that form in small blood vessels throughout the body (thrombotic microangiopathy). Red blood cells passing through the microscopic clots experience shear stress, which causes damage to the red blood cell membrane, and which in turn leads to intravascular hemolysis and schistocyte formation. Thromboses also cause reduced blood flow, which can result in end organ damage. Symptoms typically include neurological problems, such as hallucination, bizarre behavior, altered mental status, stroke, or headaches; kidney failure; fever; and thrombocytopenia (low platelet count), resulting in bruising or purpura; and microangiopathic hemolytic anemia, involving anemia and jaundice. Current therapy involves plasmapheresis to reduce circulating antibodies against ADAMTS13, and/or replenishing blood levels of the enzyme.

Therefore, a strong need exists for providing methods of purifying recombinant ADAMTS13, particularly on a commercial production scale, which may be used as a therapeutic agent. Purification of ADAMTS13 has proven difficult and various approaches have been attempted, including chromatography. A chromatographic material that binds non-ADAMTS13 protein, allowing the ADAMTS13 protein to appear in the eluate or supernatant, would provide a useful approach for purification. A chromatography material that binds ADAMTS13 protein, while non-ADAMTS13 impurities either remain in solution or bind much more strongly, also presents an attractive approach, and may be used in tandem with other approaches. The instant disclosure provides such approaches.

Furthermore, virus contaminants have posed additional challenges in the purification of ADAMTS13 proteins, as well as other proteins and recombinant proteins. One conventional approach involved treating a sample to be purified with a solvent-detergent mixture in solution. Incubation of the sample with the solvent-detergent chemicals led to deactivation of lipid-coated viruses. This in-solution treatment, however, inefficiently required transfer of the sample to at least one other vessel, e.g., to facilitate removal of the solvent-detergent chemicals after treatment. Further, some proteins including ADAMTS13 are sensitive to the solvent-detergent chemicals, resulting in aggregate formation. The instant disclosure provides an approach involving immobilization of the protein during the solvent-detergent treatment to address such problems of virus inactivation.

SUMMARY OF INVENTION

One aspect of the invention relates to a method for purifying recombinant A Disintegrin-like and Metallopeptidase with Thrombospondin Type 1 Motif 13 (ADAMTS13) protein (particularly, human ADAMTS13) from a sample comprising ADAMTS13 protein and non-ADAMTS13 impurities. It has surprisingly been found that hydroxyapatite chromatography can be used under conditions suitable for purifying ADAMTS13 protein from non-ADAMTS13 impurities. The method comprises enriching for ADAMTS13 protein by chromatographically contacting the sample with hydroxyapatite under conditions that allow ADAMTS13 protein to appear in an eluate from the hydroxyapatite. That is, the sample is subjected to chromatography with hydroxyapatite under conditions that allow the ADAMTS13 protein, preferably a substantial portion of the ADAMTS13 protein, to not bind the hydroxyapatite, while impurities are retained. In some preferred embodiments, recombinant ADAMTS13 protein is purified from supernatant collected from culturing CHO cells comprising recombinant ADAMTS13 nucleic acid. In some preferred embodiments, the percent yield in the supernatant or eluate surprisingly is 50% to 100%. The method may further comprise tandem chromatography comprising chromatographically contacting the eluate from the hydroxyapatite with a mixed mode cation exchange/hydrophobic interaction resin that binds ADAMTS13 protein. In some preferred embodiments, the percent yield ADAMTS13 after enrichment by tandem chromatography is surprisingly at least 60%.

In some embodiments, the method further comprises an optional pre-enrichment preparation step to concentrate ADAMTS13 in the sample and/or bind the ADAMTS13 protein to anion exchange resin. For example, the method may further comprise chromatographically contacting the sample with an anion exchange resin and eluting the ADAMTS13 protein from the anion exchange resin before chromatographic contact with the hydroxyapatite; and/or concentrating the ADAMTS13 protein in the sample by ultrafiltration before chromatographic contact with the hydroxyapatite; and/or stabilizing the ADAMTS13 protein by diafiltration exchange into a buffer comprising calcium ions and zinc ions before chromatographic contact with the hydroxyapatite. In some preferred embodiments, the sample is concentrated by 10-fold to 20-fold ultrafiltration, the buffer exchanged by diafiltration with a molecular cut-off of 30 kDa to a low-conductivity buffer containing calcium and zinc ions, and the ADAMTS13 bound and eluted from an anion exchange resin, such as ANX Sepharose Fast Flow, POROS 50D, or POROS 50PI, prior to tandem chromatography. The eluate pool from the anion exchange chromatography step is in some preferred embodiments diluted 1:4 with hydroxyapatite-dilution buffer to reduce conductivity to 6 mS/cm before tandem chromatography with hydroxyapatite, comprising chromatography with hydroxyapatite followed by chromatography using the eluate from the hydroxyapatite with a mixed mode cation exchange/hydrophobic interaction resin that binds ADAMTS13 protein. In some preferred embodiments, the eluate from the pre-enrichment step(s) can surprisingly provide a percent yield of at least 75%.

In some embodiments, the method further comprises an optional polishing step by cation exchange chromatography, following chromatographic contact with the hydroxyapatite or the mixed mode resin. In such embodiments, following contact with the hydroxyapatite or the cation exchange/hydrophobic interaction resin, the method may further comprise a step of preparing the ADAMTS13 protein for cation exchange by reducing buffer conductivity. In some embodiments, this preparing step is performed by ultrafiltration/diafiltration, by dialysis, and/or by gel filtration. In some embodiments where ultrafiltration/diafiltration is used, the cut-off is 10 kDa. In some embodiments, the buffer exchange is carried out by anion exchange chromatography on ANX Sepharose-FF low sub. In some embodiments where dialysis is used, the dialysis may consist of no more than 2 passes through a single dialysis module. In some preferred embodiments, the cation exchange chromatography is carried out on a Source S column or POROS S column. In some preferred embodiments, the percent yield ADAMTS13 after reducing the buffer conductivity is surprisingly at least 90%, and after polishing by cation exchange chromatography, surprisingly at least 70%.

In some embodiments, the method further comprises subjecting the ADAMTS13 protein to an optional virus inactivation step, e.g., to deactivate viruses and/or remove viruses and viral particles. In some embodiments, the virus inactivation step comprises adding a solvent-detergent mixture comprising a non-ionic detergent and an organic solvent to the ADAMTS13 protein. In some preferred embodiments, the ADAMTS13 protein is immobilized, e.g., immobilized on a cation exchange resin. In some embodiments, the solvent-detergent mixture comprises 1% TRITONX-100, 0.3% Tri-N-butyl phosphate, and 0.3% TWEEN 80; and/or solvent-detergent treatment lasts for 30 minutes at 12° C. to 16° C. Alternatively or in addition, the virus inactivation step may comprise filtering the ADAMTS13 protein with a nanofilter to remove viruses and/or viral particles. In some such embodiments, nanofiltration is carried out through a 20 N or 35 N filter, before and/or after solvent-detergent treatment. In some embodiments, the virus inactivation step is performed after the preparing step, described above, and/or after the tandem chromatography step; and/or after polishing cation exchange chromatography, described above. In some preferred embodiments, the percent yield ADAMTS13 after virus inactivation is surprisingly at least 95%.

In some embodiments, the method further comprises eluting the ADAMTS13 protein from the cation exchange resin. In some preferred embodiments, gradient elution is used, e.g., gradient elution comprising a first buffer having low salt concentration and a second buffer having higher salt concentration. In some more preferred embodiments, step elution is used, even more preferably, the step elution involves elution the ADAMTS13 protein from the resin with a storage buffer. For example, the storage buffer may have a pH of greater than 7.0 and comprise less than 10 mM calcium ions, a buffering compound, 0.05% non-ionic detergent, and a salt. In some more preferred embodiments, the method comprises no subsequent concentration or buffer exchange step, following elution from the resin with the storage buffer.

In a particularly preferred embodiment, a method for purifying recombinant ADAMTS13 protein from a sample comprising ADAMTS13 protein and non-ADAMTS13 impurities is provided, the method comprising chromatographically contacting the sample with hydroxyapatite under conditions that allow the ADAMTS13 protein to appear in an eluate or a supernatant from the hydroxyapatite; and then chromatographically contacting said eluate with a cation exchange/hydrophobic interaction resin that binds the ADAMTS13 protein, preferably as tandem chromatography.

In another particularly preferred embodiment, chromatography steps described above are preceded by chromatographically contacting the sample with an anion exchange resin and eluting the ADAMTS13 protein from the anion exchange resin; and/or concentrating the ADAMTS13 protein in the sample by ultrafiltration, and stabilizing the ADAMTS13 protein by diafiltration exchange into a buffer comprising calcium ions and zinc ions before chromatographic contact with the hydroxyapatite.

In another particularly preferred embodiment, following contact with the hydroxyapatite or the cation exchange/hydrophobic interaction resin, the method further comprises the step of preparing the ADAMTS13 protein for cation exchange by reducing buffer conductivity, wherein the preparing step is performed by ultrafiltration/diafiltration; and/or by dialysis consisting of no more than 2 passes through a single dialysis module; and/or by gel filtration.

In still another particularly preferred embodiment, the method comprises obtaining a sample from supernatant collected from culturing CHO cells comprising recombinant ADAMTS13 nucleic acid; chromatographically contacting the sample with an anion exchange resin and eluting the ADAMTS13 protein from the anion exchange resin before chromatographic contact with the hydroxyapatite; and/or concentrating the ADAMTS13 protein in the sample by ultrafiltration; and stabilizing the ADAMTS13 protein by diafiltration exchange into a buffer comprising calcium ions and zinc ions before chromatographic contact with the hydroxyapatite; followed by chromatographically contacting the sample with hydroxyapatite under conditions that allow the ADAMTS13 protein to appear in an eluate or a supernatant from the hydroxyapatite; and then chromatographically contacting the eluate with a cation exchange/hydrophobic interaction resin that binds the ADAMTS13 protein; followed by preparing the ADAMTS13 protein for cation exchange by reducing buffer conductivity, e.g., by ultrafiltration/diafiltration; and/or by dialysis consisting of no more than 2 passes through a single dialysis module; and/or by gel filtration, optionally further comprising one or more virus inactivation steps. In some such embodiments, the virus inactivation step comprises adding a solvent-detergent mixture comprising a non-ionic detergent and an organic solvent to the ADAMTS13 protein, wherein the ADAMTS13 protein is immobilized on a cation exchange resin and the solvent-detergent mixture comprises 1% TRI-TONX-100, 0.3% Tri-N-butyl phosphate, and 0.3% TWEEN 80. In still another embodiment, the virus inactivation step uses, as well as or instead of the solvent-detergent treatment, a nanofilter to remove viruses and/or viral particles. In some preferred embodiments, the percent yield ADAMTS13 of the overall procedure outlined above is surprisingly 22-24% or more, and in even more preferred embodiments, aggregates surprisingly are reduced by 50%.

In some embodiments where the ADAMTS13 has been immobilized on a cation exchange resin, the method further comprises eluting the ADAMTS13 protein from the resin using step elution with a storage buffer having a pH of greater than 7.0 and comprising less than 10 mM calcium ions, a buffering compound, 0.05% non-ionic detergent, and a salt; or using gradient elution comprising a first buffer having low salt content and a second buffer having higher salt content.

Another aspect of the invention relates to a composition comprising a recombinant ADAMTS13 protein prepared according to any embodiment of the methods described herein. In some embodiments, the composition is a pharmaceutical composition, e.g., a composition comprising purified ADAMTS13 protein and a pharmaceutically acceptable carrier.

Still a further aspect of the invention relates to a method for inactivating virus contaminants in a protein sample, where the protein may be any protein from a source that may have viral contaminants. In preferred embodiments, the protein is recombinant protein, particularly proteins sensitive to aggregation when exposed to organic solvents and detergents. In some embodiments, the protein may be ADAMTS13 protein, in particular recombinant ADAMTS13, or a different protein (in particular, a different recombinant protein). In some embodiments, the recombinant protein is a blood coagulation factor. In some embodiments, the protein is, e.g., one or more of Factor VIII, Factor II, Factor VIIa, Factor IX, thrombin, von Willebrand factor, anti-MIF antibody, or another protein being purified by chromatography. The viral inactivation may be carried out in conjunction with protein purification or not. In some embodiments, the method comprises immobilizing the protein on a support; and treating the immobilized protein with a detergent-solvent mixture comprising a non-ionic detergent and an organic solvent. In some preferred embodiments, the support is a chromatographic resin. In even more preferred embodiments, the detergent-solvent mixture comprises 1% Triton X-100, 0.3% Tri-N-butyl phosphate, and 0.3% Polysorbate 80 (Tween 80). The solvent-detergent mixture treatment can continue for a prolonged time, e.g., for 30 minutes to 1 hour, while the protein remains immobilized on the chromatographic resin, e.g., on a cation exchange resin; and/or solvent-detergent treatment may occur at 2° C. to 10° C. This approach to virus inactivation surprisingly can reduce the formation of protein aggregates during treatment with a detergent-solvent mixture by a significant amount, e.g., by more than 50%, as compared to treatment with a solvent-detergent mixture while the protein is not immobilized in solution. In some preferred embodiments, the procedure is followed by eluting the protein from the support with a buffer, such as gradient elution where small amounts of aggregates that do form are further removed in the late eluting fraction. In some preferred embodiments, the procedure is followed by eluting the protein with a storage buffer. In some more preferred embodiments, the elution buffer comprises a concentration of 0.1% Tween 80. In some even more preferred embodiments, the method comprises no subsequent concentration or buffer exchange step, following elution from the resin with the storage buffer. In some preferred embodiments, aggregates surprisingly are reduced by 50%.

In yet still another particularly preferred embodiment, a method for inactivating virus contaminants in a protein sample is provided, the method comprising: immobilizing the protein on a chromatographic resin; and treating the immobilized protein with a solvent-detergent mixture comprising 1% Triton X-100, 0.3% Tri-N-butyl phosphate, and 0.3% Polysorbate 80, for 30 minutes to 1 hour. In some such embodiments, the method further comprises eluting the protein with a storage buffer having a pH of greater than 7.0 and comprising less than 10 mM calcium ions, a buffering compound, 0.05% non-ionic detergent, and a salt.

These and other aspects of the invention are described in more detail below.

BRIEF DESCRIPTION OF THE DRAWINGS

FIGS. 2A-D depict variations in purification runs on a cation exchange column. FIG. 2A depicts a procedure involving cation exchange chromatography with step elution, following virus inactivation; FIG. 2B depicts a procedure involving cation exchange chromatography with step elution, but without a preceding virus inactivation; FIG. 2C depicts a procedure involving cation exchange chromatography with gradient elution, followed by virus inactivation on the chromatographic column; and FIG. 2D depicts a procedure involving cation exchange chromatography with gradient elution, but without a preceding virus inactivation.

DETAILED DESCRIPTION

Figure 1:
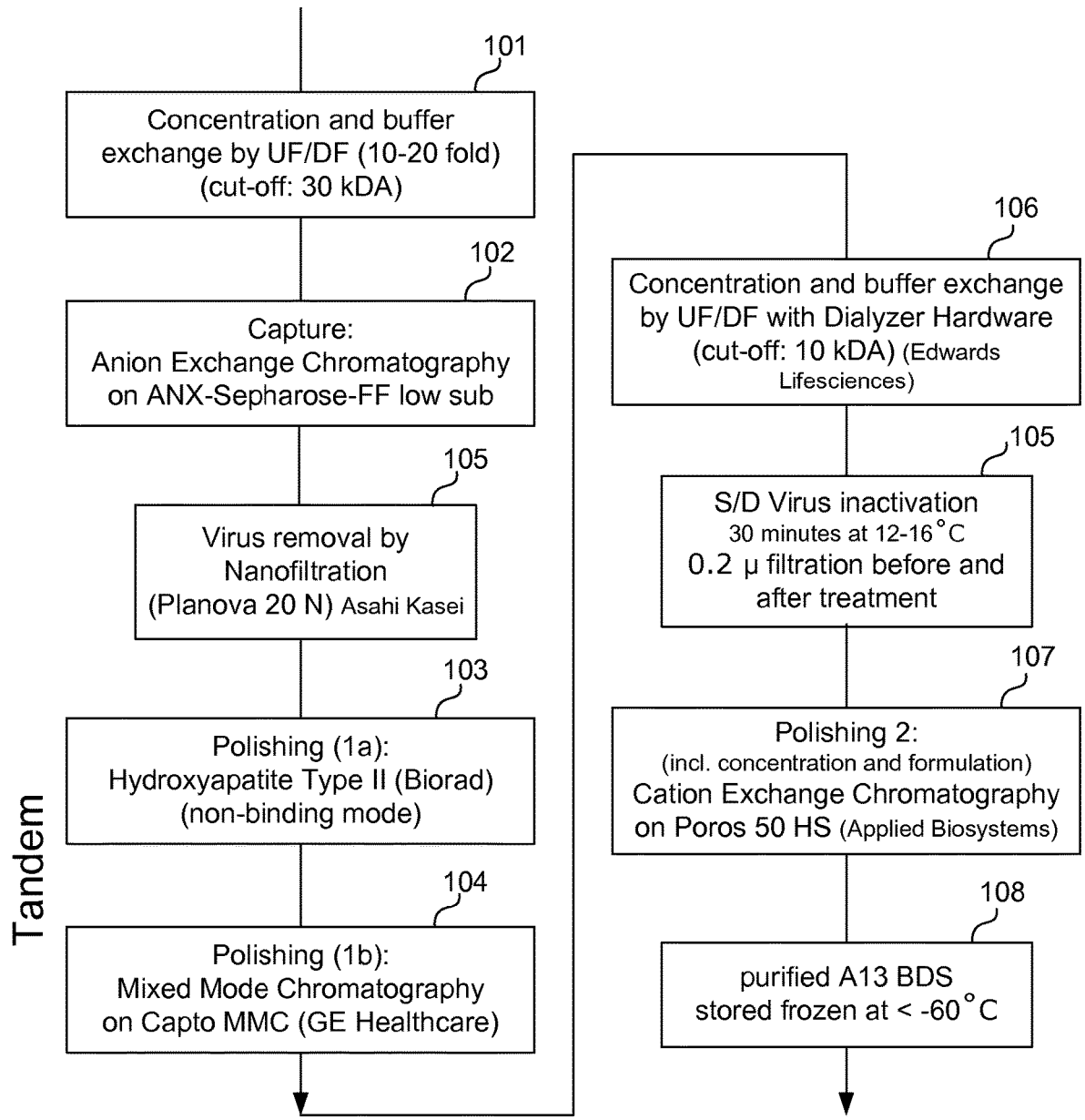
FIG. 1 depicts a flow diagram of exemplary steps of the method for purifying recombinant a disintegrin-like and metallopeptidase with thrombospondin type 1 motif 13 (ADAMTS13) from a sample comprising ADAMTS13 and non-ADAMTS13 impurities, in accordance with the instant invention. The order of the steps set forth in FIG. 1 may be re-ordered, and/or one or more steps omitted, as disclosed herein and as understood by one of skill in the art.

One aspect of the invention relates to a method for the purification of recombinant A Disintegrin-Like and Metallopeptidase with Thrombospondin Type 1 Motif 13 (ADAMTS13) protein from a sample, which may also comprise non-ADAMTS13 impurities. The protein sample may also include virus contaminants, which may be removed and/or inactivated by one or more virus inactivation steps.

As used herein "A Disintegrin-Like and Metallopeptidase with Thrombospondin Type 1 Motif 13," "ADAMTS13," "ADAMTS13 protein," "ADAMTS13 polypeptide," and "recombinant ADAMTS13" are interchangeable (unless otherwise specified) and refer to a recombinant mammalian ADAMTS13 protein, which also may be a biologically active derivative or fragment of a full-length ADAMTS13 protein. The amino acid sequence of full-length human and murine ADAMTS13 proteins have respective UniProtKB® accession numbers of Q76LX8 and Q769J6. Structural details and sequence information on human ADAMTS13 can be found in Zheng et al. ((2001) J. Biol. Chem. 276: 41059-63).

The term "biologically active derivative or fragment thereof" as used herein means any polypeptides with a biological function similar, or substantially similar, to that of ADAMTS13. The polypeptide sequences of the biologically active derivatives or fragments thereof may comprise deletions, additions, and/or substitution of one or more amino acids whose absence, presence, and/or substitution, respectively, do not have any substantial negative impact on one or more biological activities of the ADAMTS13 protein. For example, alternative splicing gives rise to a 130 kDa species that is a biologically active fragment of the full-length protein. The biological activity of said polypeptides may be measured by well-known methods, for example, methods testing the proteolytic activity of ADAMTS13 on von Willebrand Factor (vWF), and/or subsequent reduction and/or delay in downstream effects. By "downstream effects" is meant one or more biological, biochemical, or physiological manifestations of the action of ADAMTS13 protein on its native substrate(s), whether the effect is a direct cause of ADAMTS13 function, or an indirect cause thereof, e.g., an effect resulting from a cascade of events following ADAMTS13 activity. Assays include, without limitation, methods testing the reduction and/or delay of platelet adhesion to the endothelium, the reduction and/or delay of platelet aggregation, the reduction and/or delay of the formation of platelet strings, the reduction and/or delay of thrombus formation, the reduction and/or delay of thrombus growth, the reduction and/or delay of vessel occlusion, the proteolytical cleavage of vWF (e.g., FRETS-VWF73 (Peptides International, Louisville, Ky.)), and/or the disintegration of thrombi (see, e.g., U.S. Pat. No. 7,270,976, entitled "Methods for measuring ADAMTS13 activity and protein on platelets and in plasma," col. 6, line 55 to col. 10, line 34, and col. 12, line 1 to col. 18, line 25 and U.S. Pat. No. 7,468,258, entitled "Self-quenching homofluorophore compositions for detecting enzyme activity" col. 11, line 26 to col. 16, line 50; see also U.S. Patent Publication Nos. 20070015703, entitled "ADAMTS13-containing compositions having thrombolytic activity" at paragraphs [0036], [0043]-[0045], and [0053], and 20070065895, entitled "Substrates specific to von willebrand factor cleaving protease and method of assaying the activity"; and European Application No. 1990421A1, entitled "Method for Detection of Condition in Consciousness Disorder Patient and Kit for the Detection", which are incorporated herein by reference with respect to assays for ADAMTS13 polypeptides and derivatives and/or fragments thereof).

Recombinant ADAMTS13, e.g., recombinant human ADAMTS13, may be expressed by any method known in the art. One specific example is disclosed in WO 02/42441, which is incorporated herein by reference with respect to the method of preparing a recombinant ADAMTS13 nucleotide sequence (see page 14, line 6 to page 18, line 4). In some embodiments, recombinant ADAMTS13 is produced according to the following process: (i) preparing a recombinant ADAMTS13 nucleotide sequence by genetic engineering, e.g. via reverse transcription of RNA and/or amplification of DNA; (ii) introducing the recombinant ADAMTS13 nucleotide sequence into eukaryotic cells, e.g., by transfection, such as via electroporation or microinjection; (iii) cultivating the transformed cells, e.g., in a continuous or batch-wise manner; (iv) allowing the expression of recombinant ADAMTS13, e.g., constitutively or upon induction; and (v) isolating samples comprising the expressed recombinant ADAMTS13, e.g., from the culture medium or by harvesting the transformed cells; and (vi) purifying the ADAMTS13 protein from the sample, according to methods disclosed herein.

Recombinant ADAMTS13 may be produced by expression in a suitable host system, preferably an eukaryotic host system, and more preferably a system characterized in that it can produce a pharmacologically effective ADAMTS13 molecule. Examples of eukaryotic cells include, without limitation, mammalian cells, such as CHO, COS, HEK 293, BHK, SK-Hep, and HepG2. In a preferred embodiment, CHO cells are used and the cells secrete recombinant ADAMTS13 protein into the culture medium. There is no particular limitation to the reagents or conditions used for recombinantly expressing ADAMTS13 and any system known in the art or commercially available may be employed.

"Sample" as used herein refers to any composition comprising ADAMTS13 protein and non-ADAMTS13 impurities. A skilled artisan will recognize that sample as used herein may be the result of producing recombinant ADAMTS13 as described above. Accordingly, the sample may comprise supernatant collected from culturing transformed cells, which express recombinant ADAMTS13; buffers comprising ADAMTS13 at one or more steps of a process of purifying recombinant ADAMTS13 protein from culture medium; and/or transformed cells harvested from cell culture. Alternatively, the sample may be blood, plasma, or a fraction of blood or plasma.

In some embodiments, ADAMTS13 is purified from a sample comprising 100 L cell culture supernatant. However, a skilled artisan will recognize that the methods of the invention may be scaled up as appropriate, e.g., for large scale production. Accordingly, in some embodiments, the method comprises purifying ADAMTS13 protein on a commercial production scale, e.g., from an at least about 250 L sample, an at least about 500 L sample, or an at least about 1,000 L sample.

"Non-ADAMTS13 impurities" as used herein generally refers to process-related impurities. Impurities may include, e.g., host cell impurities (such as contaminating host cell proteins, also referred to as host cell antigens) and other biomolecular impurities such as DNA, RNA, and cell debris; media component(s); solvents; detergents; and the like. Additionally, non-ADAMTS13 impurities also include product-related impurities, e.g., derivatives or fragments of ADAMTS13 protein, which are not biologically active, or aggregates of ADAMTS13 protein. In the case of blood or plasma, non-ADAMTS13 impurities may include other proteins normally found in blood or plasma, e.g., albumin, immunoglobulins, etc. As used herein "aggregates" refers to structures comprising more than one ADAMTS13 polypeptide molecule, or more than one of any other protein molecule, which corresponds to high molecular weight structures or oligomeric structures, such as dimmers, trimers, and other multimers of the macromolecule. "Non-ADAMTS13 impurities" may also include virus contaminants. "Virus contaminants" refers to any impurities resulting from and/or derived from a virus, including, e.g., virus particles, virus proteins, viral DNA, viral RNA, or fragments thereof.

The terms "purifying," "purified," "to purify" and the like refer to removing, isolating, or separating ADAMTS13 from non-ADAMTS13 impurities. For example, recombinant ADAMTS13 protein expressed in plant, bacterial, yeast, or mammalian host cells may be purified by the removal of non-ADAMTS13 impurities comprising, e.g., host cell proteins. The percent purity may refer to the percent of ADAMTS13 protein versus host cell protein (e.g., CHO protein). "Substantially purified" recombinant ADAMTS13, is at least about 60% free, preferably at least about 75% free, and more preferably at least about 90% free (or about 95%, about 99%, or about 99.9% free) from non-ADAMTS13 impurities. In particular, "substantially purified" recombinant ADAMTS13 is at least about 60% free, preferably at least about 75% free, and more preferably at least about 90% free (or about 95%, about 99%, or about 99.9% free) from host cell proteins. Host cell proteins can be detected, for example, by immunochemical methods using polyclonal antisera, as discussed in more detail below.

The removal of contaminants may also result in enrichment of the ADAMTS13 protein. "Enrichment," "enriching," and "to enrich" as used herein refer to an increase in the percent of recombinant ADAMTS13 in the sample. Accordingly, enrichment of ADAMTS13 protein occurs when the percent of ADAMTS13 is increased in a sample after some manipulation of the sample, e.g., subjecting the sample to one or more chromatographic steps. In one embodiment, ADAMTS13 is sufficiently enriched when there is at least about 10-fold reduction to about 115-fold reduction of non-ADAMTS13 impurities, particularly host cell proteins. In one embodiment, ADAMTS13 is sufficiently enriched when there is at least about 20-fold (e.g., about 30-fold, about 40-fold, about 50-fold, about 60-fold, about 70-fold, about 80-fold, about 90-fold, about 100-fold, etc.) reduction of non-ADAMTS13 impurities, and in particular, the reduction occurs with respect to host cell proteins.

A skilled artisan will be able to use methods available in the art to determine the fold reduction of non-ADAMTS13 impurities, particularly host cell proteins. For example, an assay for non-ADAMTS13 impurities may be utilized. In one embodiment, the sample is conditioned supernatant collected from the cultivation of transformed cells expressing recombinant ADAMTS13 and the assay to determine fold reduction of non-ADAMTS13 impurities measures levels of host cell proteins. In one particular embodiment, the transformed cells are transformed CHO cells, and the assay is an enzyme-linked-immunosorbent serologic assay that measures CHO proteins. Fold reduction of non-ADAMTS13 impurities may be calculated, e.g., as the amount of non-ADAMTS13 impurities in the sample over the amount of non-ADAMTS13 impurities eluted, as the impurity level in a load (e.g., in ppm) divided by the impurity level in the eluate (e.g., in ppm).

Host cell proteins may be detected, e.g., by immunochemical methods using polyclonal antisera against protein components of the host cell and/or recombinant vector system used to manufacture ADAMTS13. Generally, antisera may be raised against antigen derived from the host cell, wherein the host cell comprises an expression vector that is used in the manufacturing process but that lacks the gene coding for ADAMTS13. Host cell impurities may be extracted, using the method(s) identical and/or substantially similar to those described herein. Purified (or partly purified) host cell antigens obtained using the method(s) identical and/or substantially similar to those described herein may then be used for the preparation of antisera against protein components of the host cell and recombinant vector system used to manufacture ADAMTS13. The host cell proteins can be detected using the antisera in an immunoassay, for example, in an ELISA or by western blot analysis. Host cell protein impurities may also be detected by separating the sample to be analyzed by 2D gel electrophoresis and silver staining and/or colloidal gold staining to detect proteins present. HPLC may also be used to quantify the levels of host cell impurities; however, HPLC methods are not as sensitive as the immunoassay or silver staining methods. Preferably, host cell impurities are reduced to below detectable levels using, e.g., one or more of these analytical methods.

As used herein, the term "about" denotes an approximate range of plus or minus 10% form a specified value.

Enrichment of ADAMTS13

Generally, the invention provides a method of purifying recombinant ADAMTS13 protein (preferably human ADAMTS13 protein) from a sample comprising ADAMTS13 protein and non-ADAMTS13 impurities, wherein the method comprises chromatographically contacting the sample with (i) hydroxyapatite or (ii) hydroxyapatite and a mixed mode cation exchange/hydrophobic interaction resin in tandem, so as to enrich the amount of ADAMTS13 in the sample. "Chromatographically contacting" as used herein refers to contacting a sample or other mixture to be separated with a chromatographic resin using any mode of chromatography described herein and/or known in the art. Modes include, without limitation, batch-mode and column chromatography. The contacting is effected by exposing and/or incubating the sample on, in or within the resin, filtering the sample through the resin, or by any other means. The buffer used for chromatography often is a phosphate buffer.

In some embodiments, the sample is chromatographically contacted with hydroxyapatite under conditions that allow the ADAMTS13 protein to appear in the eluate from the hydroxyapatite. By "under conditions" refers to one or more parameters or variables under which the chromatography is carried out, including, e.g., column height, packing, buffer (pH, salt concentration, ionic strength, etc), temperature, pressure, and the like. That is, the sample is subjected to chromatography with hydroxyapatite under conditions that allow ADAMTS13 protein, preferably a substantial portion of the ADMATS13 protein in the sample, to not bind to the hydroxyapatite. If column chromatography is used, the ADAMTS13 protein, preferably a substantial portion thereof, will flow through the column, thereby enriching for ADAMTS13 in buffer coming off the column, as the flow-through fraction or eluate, while non-ADAMTS13 impurities are retained. If batch chromatography is used, the supernatant or supernatant fraction will comprise the ADAMTS13 protein, or a substantial portion thereof. "Eluate" is used interchangeably herein with "flow through", "flow through fraction", "supernatant", or "supernatant fraction." The eluate (or supernatant) can be collected. Such collection occurs, e.g., by centrifugation, sedimentation, filtration, etc. of the chromatographic resin after the sample is exposed to the resin and incubation completed. The eluate (or supernatant) collected from the hydroxyapatite may be further subjected to one or more steps according to the invention.

In some embodiments, for example, the method further comprises chromatographically contacting the eluate from the hydroxyapatite with a mixed mode resin, such as a cation exchange/hydrophobic interaction resin, which binds the ADAMTS13 protein. That is, the ADAMTS13 protein sample may be subjected to tandem chromatography, first with hydroxyapatite, preferably under conditions where a substantial portion of ADAMTS13 protein does not bind the hydroxyapatite, followed by chromatography with a mixed mode cation exchange/hydrophobic interaction resin that binds the ADAMTS13 protein. Additional details regarding the hydroxyapatite chromatography step, and the optional tandem step of mixed mode chromatography, using a cation exchange/hydrophobic interaction resin, are provided below.

(a) Hydroxyapatite Chromatography

The hydroxyapatite chromatography step involves any method of chromatography with hydroxyapatite, as described herein, as known in the art, or as can be appreciated by one of skill in the art, especially in light of disclosures herein. Methods of chromatography with hydroxyapatite are well-known in the art. Hydroxyapatite has a chemical formula of $Ca_{10}(PO_4)_6(OH)_2$ and is a major constituent of bone and tooth mineral, as well as other biological structures. Hydroxyapatite may be obtained from such natural sources or may be synthesized by well-known methods. Hydroxyapatite is widely used as a chromatographic medium or support, particularly for chromatographic separations of proteins. The particle size generally is not critical and may vary widely. Typical particle sizes range from about 1 µm to about 1,000 µm in diameter, preferably from about 10 µm to about 100 µm in diameter. The porosity may also vary widely. In preferred embodiments, the average pore diameter ranges from about 100 Å to about 10,000 Å, more preferably from about 500 Å to about 3,000 Å, even more preferably 500 Å to 3,000 Å.

Various hydroxyapatite chromatographic media are available commercially, and any available form of the material can be used in the practice of the methods disclosed herein. Non-limiting examples of commercially available ceramic hydroxyapatite material that may be used include MACRO-PREP™, Hydroxyapatite Types I and II (Biorad, Hercules, Calif.), and HA ULTROGEL® (PALL, Ann Arbor, Mich.). In one embodiment, the sample is subject to chromatography with Hydroxyapatite type II (Biorad, Hercules, Calif.).

Surprisingly, it was discovered that upon chromatographically contacting a sample with hydroxyapatite, a significant or substantial portion of non-ADAMTS13 impurities in the sample bind hydroxyapatite, while a significant or substantial portion of the ADAMTS13 protein remains in solution. Accordingly, as discussed above, treatment of the sample with hydroxyapatite may be performed in batch-mode or in column chromatography mode according to well-known methods, and sufficiently enriched ADAMTS13 protein collected in the supernatant or in the eluate, respectively.

As used herein, "substantial portion" refers to a recovery yield in the supernatant or eluate of about 30% to about 100% (e.g., about 40% to about 90%, e.g., about 50% to about 80%, e.g., about 60% to about 70%) of recombinant ADAMTS13 protein from the sample compared to that prior to the hydroxyapatite chromatography step. For example, recovery yield in the supernatant or eluate of about 50% to about 100% indicates that the sample was subject to chromatography with hydroxyapatite under conditions that allow a substantial portion of ADAMTS13 protein to flow through.

In preferred embodiments, the sample to be subjected to hydroxyapatite chromatography has a low conductivity, e.g., between about 3 mS/cm and about 15 mS/cm at room temperature, preferably less than about 10 mS/cm at room temperature. In one embodiment, the sample has a conductivity of 6 mS/cm at room temperature. In another embodiment, the sample has a conductivity of 7 mS/cm at room temperature. A skilled artisan will readily appreciate that conductivity of the sample may be adjusted with a salt solution comprising neutral salts, e.g., sodium chloride, potassium chloride, sodium sulfate, sodium phosphate, potassium phosphate, and the like, and can be suitably buffered with about 20 mM phosphate buffer. The sample preferably has a pH between about 6.5 and about 9.0, and preferably, has a pH between 7 and 8. The sample may remain in contact with the hydroxyapatite for any length of time that will allow sufficient binding of non-ADAMTS13 impurities, e.g., for about 5 minutes to about 24 hours. Enriched ADAMTS13 may be collected in the supernatant fraction or the flow through fraction, which may include eluate from subsequent washes, particularly the first wash.

In one embodiment, subjecting the sample to chromatography with hydroxyapatite under conditions that allow a substantial portion of ADAMTS13 protein to remain in the supernatant or eluate results in enriched ADAMTS13, e.g., about 10-fold reduction to about 115-fold reduction of non-ADAMTS13 impurities, particularly host cell proteins, compared to the sample prior to chromatography with hydroxyapatite. In one embodiment, chromatography with hydroxyapatite reduces host cell proteins in the sample by at least about 20-fold (e.g., about 30-fold, about 40-fold, about 50-fold, about 60-fold, about 70-fold, about 80-fold, about 90-fold, e.g., about 100-fold, etc.).

In preferred embodiments, subjecting the sample to chromatography with hydroxyapatite under conditions that allow a substantial portion of ADAMTS13 protein to remain in the supernatant or eluate results in about 90% to about 99% removal of non-ADAMTS13 impurities, particularly host cell proteins. In one embodiment, subjecting the sample to chromatography with hydroxyapatite results in at least about 90% (e.g., about 91%, about 92%, about 93%, about 94%, about 95%, about 96%, about 97%, about 98%, about 99%, about 99.5%, etc.) removal of non-ADAMTS13 impurities, particularly removal of host cell proteins. Accordingly, methods disclosed herein comprising enriching for ADAMTS13 protein by subjecting the sample to chromatography with hydroxyapatite under conditions that allow a substantial portion of the ADAMTS13 protein to remain in the supernatant or eluate may also provide a buffer comprising ADAMTS13 protein that is substantially purified.

Exemplary column conditions that allow a substantial portion of ADAMTS13 to flow through a hydroxyapatite chromatography column are provided in the examples below. Generally, to allow a substantial portion of ADAMTS13 protein to flow through during chromatography with hydroxyapatite, the chromatography column preferably will have a bed height between about 5 cm to about 30 cm, e.g., 20 cm to 30 cm. Additionally, prior to subjecting the sample to chromatography with hydroxyapatite, e.g., before loading the sample onto the hydroxyapatite column, the column may first be washed, activated, and/or equilibrated respectively with well-known wash, activation, and/or equilibration buffers, particularly those suggested by the manufacturer of the hydroxyapatite. In one embodiment, the column is activated and equilibrated with the same buffer, e.g., a buffer comprising 20 mM Na/K $PO_4$, having a pH of 7.0 and having a conductivity of 5.5. mS/cm at room temperature.

(b) Mixed Mode Cation Exchange/Hydrophobic Interaction Chromatography

In one embodiment, ADAMTS13 protein is enriched by tandem chromatography with the hydroxyapatite followed by a mixed mode cation exchange/hydrophobic interaction resin that binds ADAMTS13 protein. It has been surprisingly discovered that ADAMTS13 binds the mixed mode cation exchange/hydrophobic interaction resin while non-ADAMTS13 impurities either remain in solution or bind much more strongly to the mixed mode cation exchange/hydrophobic interaction resin. Accordingly, treatment of the sample with hydroxyapatite followed by treatment with a mixed mode cation exchange/hydrophobic interaction resin may be performed in successive batch-mode or in successive column chromatography mode according to well-known methods and sufficiently enriched ADAMTS13 protein may be collected in the final supernatant fraction or final eluate pool after subjecting the sample to tandem batch-mode chromatography or tandem column chromatography, respectively. Accordingly, as described herein, ADAMTS13 protein is enriched by subjecting the sample to chromatography with hydroxyapatite under conditions that allow a substantial portion of ADAMTS13 protein to remain in the supernatant or to flow through a column comprising hydroxyapatite as the eluate. After treatment with hydroxyapatite, the collected supernatant or eluate comprising enriched ADAMTS13 optionally is subjected to batch-mode or column chromatography with a mixed mode cation exchange/hydrophobic interaction resin. In one embodiment, the supernatant or eluate from the hydroxyapatite step is fed into a chromatography column comprising the mixed mode cation exchange/hydrophobic interaction resin. Batch-mode or column chromatography with a mixed mode cation exchange/hydrophobic interaction resin can be carried out by any method described herein, known in the art, or as can be appreciated by one of skill in the art, especially in light of disclosures herein. A preferred mixed mode cation exchange/hydrophobic interaction resin, suitable for use after chromatography with hydroxyapatite, is sepharose-based matrix comprising a hydrophilic linker. The hydrophilic linker may comprise a functional ligand, e.g., via a thio-ether group. The hydrophilic ligand may be negatively-charged and may further comprise a hydrophobic group, e.g., a hydrocarbon. A hydrophilic ligand further comprising a hydrophobic group can create a mixed mode ligand, that is, a ligand with multimodal functionality, suitable for performing mixed mode chromatography, as described herein. In some embodiments, the ionic capacity of the mixed mode cation exchange/hydrophobic interaction resin may be between about 0.07 mM/mL to about 0.09 mM/mL and have a pH stability between about 2 to about 14. Generally, ADAMTS13 will bind the mixed mode cation exchange/hydrophobic interaction resin via ionic, hydrogen, and/or hydrophobic bonds.

Examples of commercially available mixed mode cation exchange/hydrophobic interaction resins that may be used in accordance with the methods described herein include, without limitation, CAPTO™ MMC medium (GE Healthcare) and SampliQ SAX (Agilent Technologies, Santa Clara, Calif.). In a preferred embodiment, the mixed mode cation exchange/hydrophobic interaction resin is CAPTO™ MMC. CAPTO™ MMC is a multimodal weak cation exchanger based on rigid, highly cross-linked, beaded agarose with a mean particle size of about 75 μm. It comprises ligands with multimodal functionality that bind proteins at high salt concentrations. It has a typical flow velocity of about 600 cm/h for an about 1 m diameter column, with about 10 cm to about 20 cm bed height at about 20° C., using process buffers with the about same viscosity as water at less than about 3 bar (about 0.3 MPa).

During chromatography with a mixed mode cation exchange/hydrophobic interaction resin, ADAMTS13 binds to the mixed mode cation exchange/hydrophobic interaction resin and is further isolated from non-ADAMTS13 impurities (e.g., host-cell proteins present in the sample pre-enrichment). Where the mixed mode chromatography step is performed on a column, the cation exchange/hydrophobic interaction resin absorbs ADAMTS13 protein, while contaminating non-ADAMTS13 impurities are removed from the process stream and separated from the ADAMTS13 protein in the sample by flowing through the chromatography column.

The mixed mode cation exchange/hydrophobic interaction resin to which ADAMTS13 is adsorbed is then washed, e.g., to remove loosely-bound contaminants or impurities and/or to adjust buffer conductivity in preparation for elution of ADAMTS13 from the resin. That is, after the sample is chromatographically contacted with hydroxyapatite, and the collected supernatant or eluate comprising ADAMTS13 is chromatographically contacted with mixed mode cation/hydrophobic interaction resin and adsorbed thereto, the mixed mode cation/hydrophobic interaction resin is washed with wash buffer. Generally, the wash buffer will comprise a buffering ion phosphate and a neutral salt and will have a high pH such that binding of ADAMTS13 to the mixed mode cation/hydrophobic interaction resin is weakened as relevant parameters of the buffer are increased, e.g., with increasing salt concentration and/or pH of the buffer. In one embodiment, the ADAMTS13-bound mixed mode cation/hydrophobic interaction resin is first washed with an equilibration buffer, e.g., an equilibration buffer comprising about 20 mM phosphate and about 25 mM NaCl and having a pH of about 7.0 at room temperature. Subsequent washes may be performed with a wash buffer, comprising, e.g., about 20 mM phosphate, about 80 mM NaCl and having a pH of about 8.0 at room temperature. The ADAMTS13-bound mixed mode cation/hydrophobic interaction resin may be subject to a final wash with a buffer comprising, e.g., 50 mM Na/K $PO_4$ and 160 mM NaCl, and having a pH of 8.0, and a conductivity of 16.5 mS/cm at room temperature.

After hydroxyapatite chromatography, followed by mixed mode chromatography with a cation exchange/hydrophobic interaction resin that binds ADAMTS13 protein, and optional washing, recombinant ADAMTS13 protein is eluted from the mixed mode chromatography resin with an elution buffer. Generally, the elution buffer will comprise about 5 mM to about 100 mM buffering ions, e.g., 20 mM to 50 mM buffering ions. Exemplary buffers include, but are not limited to, phosphate, tris, HEPES, imidazole, histidine, MES, citrate, Gly-Gly, tris/acetate, and the like. The elution buffer also generally comprises monovalent or divalent cations, such as, but not limited to, sodium, potassium, or calcium ions, preferably at high concentrations in salt form (e.g., with Cl, $PO_4$, $SO_4$, or OAc anions, and the like.). In a preferred embodiment, the elution buffer comprises sodium ions at high concentration, e.g., at greater than about 700 mM $Na^+$. The elution buffer may have a pH ranging from about 7 to about 11. In one embodiment, the elution buffer comprises 50 mM Na/K $PO_4$, 1,000 mM NaCl and has a pH of 8.0 and a conductivity of 93 mS/cm at room temperature.

Exemplary conditions that allow enriched ADAMTS13 obtained from a hydroxyapatite column to bind to a mixed mode cation exchange/hydrophobic interaction resin in a column and to be isolated from non-ADAMTS13 impurities are provided in the examples below. Generally, the bed height of the mixed mode cation exchange/hydrophobic chromatography column may be about 1 cm to about 100 cm, or even higher depending on the sample volume. Further, the ratio of the hydroxyapatite chromatography column volume to the column volume of the mixed mode cation exchange/hydrophobic interaction chromatography column may be about 10:1, depending, e.g., on amounts of non-ADAMTS13 impurities in the sample compared to the amount of ADAMTS13.

Additionally, a skilled artisan will recognize that, for embodiments comprising tandem chromatography with hydroxyapatite and a mixed mode cation exchange/hydrophobic interaction resin, the resins and buffers used for washing, activation, and/or equilibrating will in certain embodiments be selected to be compatible with both columns. In one embodiment, the columns are activated separately. In another embodiment, the columns are equilibrated, loaded, and washed once in tandem, followed by one or more second or subsequent wash(es) and elution(s) applied only to the mixed mode cation exchange/hydrophobic interaction resin. In one embodiment, the buffers for activating and equilibrating the mixed mode cation exchange/hydrophobic interaction chromatography column are the same as those used to activate and equilibrate the hydroxyapatite column. In one embodiment, the buffer for activating and equilibrating the mixed mode cation exchange/hydrophobic interaction chromatography column is a buffer comprising 20 mM Na/K PO$_4$ and having a pH of 7.0 and a conductivity of 5.5. mS/cm at room temperature.

In preferred embodiments, the sample is subjected to tandem chromatography with hydroxyapatite and mixed mode cation exchange/hydrophobic interaction resins under conditions that allow a substantial portion of ADAMTS13 protein to flow through the hydroxyapatite resin, followed by being bound and then eluted from the mixed mode cation exchange/hydrophobic interaction resin. In more preferred embodiments, this tandem chromatography results in sufficiently enriched ADAMTS13. In some embodiments, subjecting a sample, e.g., conditioned supernatant collected from the cultivation of transformed host cells expressing recombinant ADAMTS13, which may be pre-enriched, to the tandem chromatography described herein yields about 40% to about 80% ADAMTS13 (e.g., between about 45% to about 75%, e.g., between about 50% to about 70%, e.g., about 55% to about 65%) and/or about 40% to about 90% activity (e.g., between about 45% to about 85%, e.g., between about 50% to about 80%, e.g., about 55% to about 75%).

In some embodiments, the tandem chromatography removes about 90% to about 99% host cell impurities. In one embodiment, tandem chromatography as described herein increases the purity of ADAMTS13 by at least about 600 fold, e.g., by at least about 650-fold, e.g., by at least about 700-fold, e.g., by at least about 800-fold, e.g., by at least about 900-fold, e.g., by at least about 1,000-fold, e.g., by at least about 1,100-fold, e.g., by at least about 1,200-fold, e.g., by at least about 1,300-fold, e.g., by at least about 1,400-fold, or by at least about 1,500-fold compared to the purity of ADAMTS13 prior to subjecting the sample to tandem chromatography.

In some embodiments, subjecting a sample, e.g., conditioned supernatant collected from the cultivation of transformed host cells expressing recombinant ADAMTS13, which may be pre-enriched, preferably by UF/DF and/or anion exchange, to the tandem chromatography described herein results in a sample with about 600 to about 1,500 ppm non-ADAMTS13 impurities (e.g., host cell antigens). For example, the tandem chromatography may result in a sample with about 750 to about 1250 ppm non-ADAMTS13 impurities, preferably a sample with less than about 1,000 ppm non-ADAMTS13 impurities.

In some embodiments, the tandem chromatography results in an about 1,000-fold reduction to an about 3,000-fold reduction of non-ADAMTS13 impurities (in particular, host cell antigens) compared to the sample prior to the tandem chromatography. In some embodiments, subjecting conditioned supernatant collected from the cultivation of transformed host cells expressing recombinant ADAMTS13, which may be pre-enriched, to the tandem chromatography described herein reduces non-ADAMTS13 impurities (e.g., host cell antigens) by at least about 1,000-fold, e.g., by at least about 1,300-fold, e.g., by at least about 1,500-fold, e.g., by at least about 2,000-fold, e.g., by at least about 2,500-fold, e.g., by at least about 3,000-fold, etc.

Accordingly, in preferred embodiments, the elution buffer from the mixed mode cation exchange/hydrophobic interaction resin, which comprises recombinant ADAMTS13, provides a composition comprising ADAMTS13 protein that is substantially purified.

Pre-Enrichment Preparation of the Sample

In some embodiments, the method disclosed herein further comprises preparing the sample comprising ADAMTS13 for enrichment by chromatography with hydroxyapatite or tandem chromatography with hydroxyapatite and mixed mode cation exchange/hydrophobic interaction resin. In this optional pre-enrichment step, the ADAMTS13 in the sample may be either or both (a) concentrated by ultrafiltration/diafiltration (UF/DF); and/or (b) chromatographically contacted with an ion exchange resin, to which ADAMTS13 binds and from which it subsequently is eluted.

(a) Pre-Enrichment Ultrafiltration/Diafiltration (UF/DF)

In an optional pre-enrichment step, ADAMTS13 in a sample is concentrated by pre-enrichment ultrafiltration, and the buffer of the sample exchanged by diafiltration. The pre-enrichment ultrafiltration/diafiltration step typically is performed prior to enrichment of ADAMTS13 by chromatography with hydroxyapatite or tandem chromatography with hydroxyapatite followed by a mixed mode cation exchange/hydrophobic interaction resin as described above. The pre-enrichment ultrafiltration/diafiltration step typically is performed prior to any pre-enrichment anion exchange chromatography (if performed). This pre-enrichment ultrafiltration/diafiltration (UF/DF) step may be effective in removing small-molecular weight components, e.g., small-molecular weight components of the cell culture media. Such components may bind to a subsequent chromatography column and decrease the capacity of the column for ADAMTS13. Accordingly, pre-enrichment UF/DF can optimize loading for later chromatography steps. In one embodiment, small-molecular weight components below about 30 kDa are removed, or at least a substantial portion thereof. In some embodiments, small-molecular components removed (or substantially removed) are components of below about 60 kDa, below about 55 kDa, below about 50 kDa, below about 45 kDa, below about 40 kDa, below about 35 kDa, below about 30 kDa, below about 25 kDa, below about 20 kDa, etc.

The pre-enrichment ultrafiltration/diafiltration step also is used in certain embodiments to exchange ADAMTS13 into an appropriate buffer solution for subsequent processing and/or to further concentrate the sample. In one embodiment, the appropriate buffer solution is a low conductivity buffer appropriate for pre-enrichment anion exchange chromatography, if such anion exchange chromatography is to be performed. For example, the low conductivity buffer will have a conductivity of less than about 10 mS/cm, e.g., about 7 mS/cm to about 8 mS/cm, e.g., 7 mS/cm at room temperature, and may have a pH equal to or greater than about 7.0.

In another embodiment, the appropriate buffer solution is an enrichment buffer appropriate for enrichment by chromatography with hydroxyapatite, which may be followed with chromatography on a mixed mode cation exchange/hydrophobic interaction resin. For example, the enrichment buffer may comprise 20 mM Na/K PO$_4$ and have a pH of about 7 at room temperature. In another embodiment, the appropriate buffer solution also comprises calcium and/or zinc ions, either or both of which stabilize ADAMTS13 protein. In one embodiment, the appropriate buffer solution comprises calcium ions at a concentration of less than about 10 mM, e.g., 2 mM. In another embodiment, the appropriate buffer solution is supplemented with zinc ions at a concentration of less than about 50 μM, e.g., 5 μM.

In some embodiments, the appropriate buffer solution comprises a buffering agent that has buffering capacity in solutions with a pH equal to or greater than about 7.0. In one embodiment, the buffering agent is selected from the group consisting of phosphate, tris, HEPES, imidazole, histidine, MES, citrate, Gly-Gly, Tris/acetate, etc.

The sample obtained after this pre-enrichment UF/DF step may be used in subsequent purification steps, e.g., the sample may be a UF/DF concentrated pool comprising host cell proteins to be removed by chromatography with hydroxyapatite, or hydroxyapatite chromatography followed by mixed mode chromatography on a cation exchange/hydrophobic interaction resin. In some embodiments, the sample following the pre-enrichment UF/DF step has been concentrated by about 10 fold to about 20 fold, e.g., by about 15 fold, compared to the sample before the pre-enrichment UF/DF step.

(b) Pre-Enrichment Anion Exchange Chromatography

Another optional pre-enrichment step comprises pre-enrichment chromatography, which may be performed prior to enrichment of ADAMTS13 by chromatography with hydroxyapatite or tandem chromatography with hydroxyapatite followed by a mixed mode cation exchange/hydrophobic interaction resin. A skilled artisan will recognize that the pre-enrichment chromatography may be performed after the optional pre-enrichment ultrafiltration/diafiltration step. Alternatively, the pre-enrichment chromatography may be performed by itself, i.e., without the optional pre-enrichment ultrafiltration/diafiltration step.

In some embodiments, the pre-enrichment chromatography step comprises chromatographically contacting the sample comprising ADAMTS13 with an anion exchange resin and eluting the ADAMTS13 protein from the anion exchange resin. That is, the ADAMTS13 is bound to an anion exchange resin and subsequently eluted therefrom. As used herein, the term "anion exchange resin" refers to any resin suitable for anion exchange chromatography and that has a net positive charge, e.g., due to a positively-charged group (at neutral pH). Examples include, but are not limited to, diethylaminoethane (DEAE), dimethylethanolamine (DMAE), polyethyleneimine (PEI), quaternary aminoethane (QAE), trimethylaminoethyl (TMAE), quaternary ammonium (Q), and the like, and combinations thereof.

In one embodiment, the anion exchange resin also has one or more of the following features: large pores, perfusion flow behavior, and convective flow behavior. Non-limiting examples of commercially available anion exchange resins that may be used in the pre-enrichment step disclosed herein include Q-Sepharose Fast Flow (GE Healthcare, Piscataway, N.J.), ANX-Sepharose Fast Flow low sub (GE Healthcare), DEAE-Sepharose Fast Flow (GE Healthcare), DEAE-Toyopearl (Tosoh Bioscience LLC, Grove City, Ohio), QAE-Toyopearl (Tosoh Bioscience LLC), POROS® Q (Applied Biosystems, Foster City, Calif.), POROS® 50D (Applied Biosystems), POROS® 50PI (Applied Biosystems), Convective Interaction Media (CIM®; BIA Separation), Fractogel-DMAE (Capitol Scientific Inc., Austin, Tex.), Fractogel EMD-TMAE (Capital Scientific Inc., Austin, Tex.), Matrex Cellufine DEAE (Chisso Corp., Rye, N.Y.), and the like.

During pre-enrichment anion exchange chromatography, ADAMTS13 binds to the anion exchange resin and is isolated from non-ADAMTS13 impurities (e.g., host-cell components that may be present in the pre-enrichment UF/DF concentrated pool). Generally, the anion-exchange resin absorbs ADAMTS13 protein, while non-ADAMTS13 impurities with isoelectric points greater than the operating pH are removed from the process stream by flowing through the anion exchange column. Non-ADAMTS13 impurities with isoelectric points below the operating pH bind more strongly, preferably much more strongly, to the resin, such that they preferably do not co-elute with the ADAMTS13 protein. The column to which ADAMTS13 is adsorbed is then washed prior to elution, e.g., to remove loosely-bound impurities or contaminants and/or to adjust the conductivity of the buffer in preparation for elution. Typically, bound ADAMTS13 is eluted from the anion exchange resin by increasing the ionic strength of the buffer. In one embodiment, ADAMTS13 is eluted by step elution. Generally, the loaded sample and wash buffer have a pH of between about 7 to about 9, e.g., 7.7, and a conductivity of less than about 10 mS/cm (e.g., 6.5 mS/cm) at room temperature. The elution buffer(s) may have a pH of about 6 to about 9 (e.g., 7) and have a conductivity of greater than about 10 mS/cm (e.g., 16.5 mS/cm) at room temperature.

Typically, the eluate from the anion exchange chromatography step yields about 60% to about 120% ADAMTS13 activity (e.g., yields about 70% or about 80% to about 107% ADAMTS activity) and/or comprises recombinant ADAMTS13 with a purity of about 20% to about 70%, (e.g., a purity of about 30%, about 40%, about 50%, about 60%, etc). In one embodiment, anion exchange chromatography reduces non-ADAMTS13 impurities by about 2-fold to about 5-fold. In a preferred embodiment, the percent yield after pre-enrichment preparation can be about 75%.

The eluted ADAMTS13 may then be enriched by subjecting the sample to chromatography with hydroxyapatite that allows a substantial portion of ADAMTS13 protein to flow through or subjecting the sample to tandem chromatography with hydroxyapatite under conditions that allow a substantial portion of ADAMTS13 protein to flow through, followed by chromatography with a mixed mode cation exchange/hydrophobic interaction resin that binds ADAMTS13 protein, as described above.

Virus Inactivation

A skilled artisan will recognize that methods of virus inactivation may be particularly useful in purifying recombinant ADAMTS13 from samples that comprise or potentially comprise virus contaminants (impurities resulting from and/or derived from viruses, including, e.g., virus particles, virus protein, viral DNA, viral RNA, and fragments thereof). Accordingly, in one embodiment, the method disclosed herein further comprises at least one virus inactivation step. The term "virus inactivation" refers to either or both the situation wherein viruses are maintained in the solution but are deactivated or inactivated (e.g., rendered non-viable, for example, by dissolving the lipid coat of lipid-enveloped viruses); and to the physical removal of the viruses and/or virus contaminants from the sample (for example, by size exclusion). Thus, in the context of the disclosure herein, "virus inactivation" refers to either or both viral deactivation and viral removal.

If performed, virus inactivation may occur once or more than once throughout the entire purification process. Additionally, it may occur prior or subsequent to subjecting the sample to chromatography with hydroxyapatite. In some embodiments, virus inactivation occurs prior and subsequent to the optional step of polishing by cation exchange chromatography, described in more detail below. However, a skilled artisan will recognize that virus inactivation may optionally occur, if at all, at any step during the purification process. Further, a skilled artisan can recognize the appropriate timing for virus inactivation.

Methods of rendering lipid-enveloped viruses non-viable are well-known in the art. Generally, methods of deactivating (or inactivating) lipid-enveloped viruses in a sample comprise adding a solvent-detergent mixture to the sample (see, e.g., Edwards, et al. (1987) "Tri(n-butyl) phosphate/detergent treatment of licensed therapeutic and experimental blood derivatives" Vox Sang 52: 53-59 (see especially pages 54-55); and U.S. Pat. No. 4,540,573 (col. 7, line 9 to col. 12, line 42); U.S. Pat. No. 4,764,369 (col. 7, line 17 to col. 12, line 47); U.S. Pat. No. 4,939,176 (col. 3, line 59 to col. 10, line 14); U.S. Pat. No. 5,151,499 (col. 2, line 59 to col. 11, line 38); U.S. Pat. No. 6,090,599 (col. 4, line 20 to col. 8, line 67); U.S. Pat. No. 6,468,733 (col. 5, line 12 to col. 9, line 36); and U.S. Pat. No. 6,881,573 (col. 5, line 63 to col. 14, line 9); each of which is incorporated herein by reference). The solvent-detergent combination used to deactivate lipid-coated viruses may be any solvent-detergent combination known in the art and preferably comprises a non-ionic detergent and an organic solvent. Non-limiting examples include Tri-N-butyl phosphate (TnBP) and TRITON X-100™, as well as TWEEN 80™ (CAS 9005-65-6), polyoxyethylene sorbitan monooleate, sodium cholate, and the like. The concentration of the solvent(s) and/or detergent(s) may be those commonly used in the art, for example, greater than about 0.1% TnBP and greater than about 0.1% TRITON X-100™.

In some embodiments, the conditions under which the solvent-detergent mixture inactivates the viruses comprise about 10 to about 100 mg/ml of solvent-detergent, at a pH level ranging from about 5 to about 8, and a temperature ranging from about 2° C. to about 37° C., preferably from about 12° C. to about 25° C., for about 30 minutes to about 24 hours, preferably about 30 minutes to about 1 hour. In some embodiments, the mixture is slightly shaken or stirred during the treatment. In one embodiment, the virus inactivation step comprises adding a solvent-detergent mixture (e.g., as solvent-detergent mixture comprising 0.3% TnBP, 1% TRITON X-100™, and 0.3% TWEEN 80™) to the sample for at least 1 hour, at 15° C. to 25° C. In another embodiment, the sample is treated with a solvent-detergent mixture comprising 0.3% TnBP, 1% TRITON X-100™, and 0.3% TWEEN 80™ for 30 minutes at 12° C. to 16° C. Other solvent-detergent combinations and/or suitable conditions may be used, as will be apparent to one versed in the art, such as combinations of polysorbate or cholate and tri-n-butyl phosphate. Such combinations may require longer treatment times, e.g., 2 hours, 3 hours, 4 hours, 5 hours, 6 hours, 7 hours, 8 hours, or more.

Inactivation can be brought about by any means known in the art. For example, inactivation can be stopped by dilution, preferably by dilution with cold dilution buffer. For example, in some embodiments, inactivation is stopped by dilution with one volume of cold dilution buffer comprising about 20 mM MES, and having a pH of about 6 at room temperature.

After deactivating lipid-coated viruses with the solvent-detergent combination, the solvent-detergent mixture may be removed. For example, the solvent-detergent mixture may be removed via chromatography or other suitable means. In some embodiments, chromatography with a solvent-detergent removal (SDR) resin is used, such as, e.g., HyperD™ resin (Biosepra Inc., MA) (see, e.g., U.S. Pat. No. 6,468,733 (col. 5, line 12 to col. 9, line 36), incorporated herein in its entirety by reference).

Inactivating Virus Contaminants with Immobilized Protein

In some embodiments, virus inactivation comprises viral deactivation with solvent-detergent while the protein is immobilized. Such a procedure may be used in virus inactivation of the ADAMTS13 polypeptide described herein, as well as for other proteins. Other proteins may include, without limitation, any protein or biologic from a source that may have viral contaminants, including immune system proteins (antibodies, monoclonal antibodies, fusion proteins, Fc fusions, major histocompatibility antigens, T cell receptor), enzymes (oxidoreductases, transferases, hydrolases, lyases, isomerases, ligases), structural proteins, fibrous proteins (such as cytoskeletal proteins, like actin, Arp2/3, coronin, dystrophin, keratin, myosin, spectrin, Tau protein, tubulin and extracellular matrix proteins, like collagen, elastin, F-spondin), globular proteins, plasma proteins (serum albumin and serum amyloid P component), coagulation factors (like complement proteins, Factor VIII, Factor XIII, fibrin, protein C, protein S, protein Z, protein Z-related protease inhibitor, thrombin, von Willebrand Factor), C-reactive protein, hemoproteins, cell adhesion proteins (cadherin, ependymin, integrin, NCAM, selectin), transmembrane transport proteins (CFTR, glycophorin D, scramblase), ion channels (acetylcholine receptor potassium channel), synport/antiport proteins (glucose transporter), hormones and growth factors (epidermal growth factor insulin, insulin-like growth factor, oxytocin), receptors (transmembrane receptors, G-protein-coupled receptor, rhodopsin, intracellular receptors like estrogen receptor), DNA-binding proteins (histones), transcription regulation proteins (c-myc FOXP2, FOXP3, MyoD, p53), nutrient storage/transport proteins (ferritin), chaperone proteins, macromolecular complexes (nucleosome, ribonucleoprotein, signal recognition particle, spliceosome), and the like. In preferred embodiments, the protein is recombinant protein, particularly proteins sensitive to aggregation when exposed to organic solvents and detergents. In some embodiments, the protein is ADAMTS13 protein, in particular recombinant ADAMTS13, or a different protein (in particular, a different recombinant protein). In some embodiments, the recombinant protein is a blood coagulation factor. In some embodiments, the protein is, e.g., one or more of Factor VIII, Factor II, thrombin, Factor VIIa, Factor IX, von Willebrand factor, anti-MIF antibodies, and in particular proteins amenable to chromatographic purification and/or proteins sensitive to treatment with solvent-detergent. Accordingly, another aspect of the instant invention is directed at virus inactivation of an immobilized protein. Preferably, virus inactivation is carried out in conjunction with a protein purification procedure, such that the procedure involves virus inactivation of a protein preparation by immobilizing the protein being purified.

The conventional solvent-detergent virus inactivation step applied in downstream processes for purifying various proteins, such as those described above, generally involves adding the solvent-detergent mixture in solution to the sample being purified, e.g., in a batch procedure. In the batch procedure, a sample comprising the protein is treated with the solvent-detergent mixture (e.g., a mixture comprising about 1% Triton X-100, about 0.3% tri-N-butyl phosphate, and about 0.3% Polysorbate 80) in a stirred vessel (e.g., a tank for large scale purifications). After dissolution of the solvent-detergent chemicals, the treated sample solution can be pumped into a second stirred vessel, where by definition the actual virus inactivation takes place, as here the protein solution is incubated to allow such deactivation to take place (e.g., for about 30 minutes to about one hour).

In contrast, some embodiments of the instant invention involve virus inactivation of a composition comprising a protein, e.g., a protein being purified, where the protein is immobilized. The process comprises contacting the composition comprising the protein of interest with a solvent-detergent mixture while the protein is immobilized, rather than the target protein being in solution. In preferred embodiments, the protein is immobilized on a chromatographic resin. Virus inactivation where the protein is immobilized on a chromatographic resin, e.g., on a chromatographic column, is referred to herein as "on-column" virus inactivation. The purification of ADAMTS13 on Poros S, described in the Examples below, provides one embodiment of this process, where virus inactivation is carried out on-column. One of skill in the art will recognize that the protein may be immobilized onto various supports, by a variety of means. For example, protein may be bound to any solid or semi-solid support, including a glass slide, beads, matrix, or membranes. Immobilization may result from any process whereby the protein is fixed to the support relative to other components of the protein solution. Immobilization may occur due to one or more types of bonds between the groups on the support and groups on the protein, such as, e.g., by covalent linkage, hydrogen bonds, electrostatic interactions, van der Wasls forces, and the like, or combinations thereof.

Virus inactivation of immobilized protein on a chromatographic column can simplify purification. For example, rather than requiring more than one vessel (such as a two tank system used in large scale purifications), chromatographic purification and virus inactivation may be carried out in the same vessel, e.g., on the same chromatographic column. This simplifies the downstream processes of protein purification, e.g., reducing time, conserving reagents, and/or increasing efficiency. In some embodiments, the chromatographic column is a cation exchange resin. In some embodiments, the chromatographic column is an anion exchange resin.

An additional and surprising benefit of certain embodiments of virus inactivation of immobilized protein is the reduction in aggregate formation. Some proteins show sensitivity towards solvent-detergent mixtures, e.g., forming aggregates when contacted with the solvent-detergent reagents in solution. Without being limited to a particular theory or hypothesis, contacting the sensitive protein with the solvent-detergent mixture while it is immobilized, e.g., while the protein is bound to a chromatographic resin, can prevent the formation of aggregates based simply on the physical inability of the immobilized protein molecules to contact each other. In some embodiments, the inactivation results in the formation of less than about 20% aggregates, less than about 18%, less than about 15%, less than about 12%, less than about 10%, or less than about 5% aggregates. And, in certain embodiments, the level of aggregation is reduced by at least about 10%, about 20%, about 50% or about 100% as compared to the level of aggregation when the protein preparation is subjected to virus inactivation where the protein is not immobilized.

In one preferred embodiment, the protein is loaded onto a chromatographic resin and the solvent-detergent treatment is used as a wash step, preferably a wash step that continues for a long enough incubation period to allow inactivation of lipid-enveloped viruses. For example, the wash step preferably continues for about 30 minutes to about one hour. The solvent-detergent mixture will comprise non-ionic detergent and organic solvent at concentrations suitable to effect such virus inactivation, as described above. For example, in some embodiments, the solvent-detergent mixture comprises 1% Triton X-100, 0.3% tri-N-butyl phosphate, and 0.3% Polysorbate80. Additional details for some particular embodiments are provided below, with respect to ADAMTS13 purification.

Virus inactivation may also comprise viral removal, e.g., by filtration, such as nanofiltration using a nanofilter. Such viral removal may occur alone, or in combination with viral deactivation (inactivation), e.g., the viral deactivation step comprising treatment with a solvent-detergent mixture as described above. When virus inactivation comprises both viral deactivation and viral removal, viral removal may occur prior to and/or subsequent to the viral deactivation by solvent-detergent treatment. Generally, viral removal from a sample involves filtering the sample, e.g., passing the sample through a filter having a pore size that maintains ADAMTS13 in the sample, while allowing viruses and virus contaminants to flow through. In one embodiment, the pore size of the filter is between about 15 nm and about 50 nm. Filtration also can be carried out by nanofiltration using a 20 N or 35 N filter (Planova, Asahi Kasei). In some embodiments, pre-filters are used to prevent fouling the nanofilter, e.g., an about 2 µM filter, or a 0.2 g PVDF or PES membrane may be used Polishing by Cation Exchange Chromatography In some embodiments, the method further comprises, after chromatography with hydroxyapatite (or tandem chromatography with hydroxyapatite followed by a mixed mode cation exchange/hydrophobic interaction resin), the optional step of polishing the sample comprising ADAMTS13 by chromatography on a cation exchange resin. In this step, the conductivity of the buffer comprising ADAMTS13 may be reduced prior to polishing, if necessary to achieve an appropriate conductivity for the cation exchange chromatography.

(a) Reducing Buffer Conductivity

After chromatography with hydroxyapatite or tandem chromatography with hydroxyapatite followed with a mixed mode cation exchange/hydrophobic interaction resin, the buffer comprising ADAMTS13 protein may be prepared for cation exchange by reducing the conductivity of the buffer, e.g., by removing ionic components (e.g., sodium chloride). In some embodiments, buffer conductivity is reduced to less than about 5 mS/cm and/or the pH is reduced to about 6.0. The conductivity of the buffer may be reduced by any method known in the art, described herein, or as can be appreciated by one of skill in the art, especially in light of the disclosures herein. Non-limiting examples include ultrafiltration/diafiltration (e.g., with crossflow cassettes or hollowfiber modules), gel filtration, dialysis, etc.

In one embodiment, the ADAMTS13 protein is prepared for cation exchange by ultrafiltration/diafiltration with a membrane having an about 10 kDa cut-off, against a cation exchange equilibration buffer (e.g., a buffer comprising 20 mM MES, pH 6.0 at room temperature). In some embodiments, the ultrafiltration/diafiltration membrane is a PES membrane, having an about 10 kDa to an about 50 kDa cutoff, e.g., an about 20 kDa cutoff, an about 30 kDa cutoff, an about 40 kDa cut-off, etc. Using such an approach, the buffer pH may be reduced from about 8.0 to about 6.0; and/or the conductivity of the buffer may be reduced to below about 2 mS/cm at room temperature. In some such embodiments, the buffer for the diafiltration may comprise 20 mM MES and may have a pH of 6.0 at room temperature and/or a conductivity of 0.6 mS/cm at room temperature. In some embodiments, the conductivity of the buffer for diafiltration may be identical, or substantially identical, to the cation exchange equilibration buffer to be used.

In one embodiment, preparing the buffer comprising ADAMTS13 for cation exchange is performed by dialysis, e.g., using dialyzer hardware comprising hemodialysis modules, such as a hollowfiber hemodialysis module (Aquamax series, PES chemistry of the Hollowfibers, Edwards Lifesciences, Unterschleiheim, Germany). Generally, about 2 m$^2$ of filter area is used for about 5 L of sample; and the sample buffer and dialysis buffer are run in reverse flow with respect to each other. In some embodiments, the dialysis consists of no more than two passes through a single dialysis module. By "single dialysis module" is meant one unit or structure through which dialysis is performed. A dialysis module generally comprises an open-ended bundle of hollow fiber membrane potted in a tubular housing to create two distinct flow chambers, lumen and extracapillary, each with inlet and outlet port access. A semi-permeable hollow fiber membrane separates the two chambers and selectively permits passage based on size and concentration gradient of solutes while restricting other solutes from passing between the 2 chambers. By operating the module in a counter-current flow mode, the solutes passing through the membrane are quickly swept away and diluted into a large volume of dialysate solution ("sweep"), maintaining the largest concentration gradient possible. Accordingly, dialysis may be performed in a single pass sweep through a single dialysis module.

In some embodiments, a combination of these approaches is used, e.g., UF/DF with dialysis may be used to effect concentration of the sample and buffer exchange in preparation for polishing by cation exchange chromatography. In still other embodiments, buffer exchange may be carried out by anion exchange chromatography.

(b) Cation Exchange Chromatography

As indicated above, the method disclosed herein may optionally comprise polishing the sample by chromatography on a cation exchange resin. As used herein, the term "cation exchange resin" refers to any resin suitable for cation exchange chromatography and that has a net negative charge, e.g., due to a negatively-charged group (at neutral pH). Examples include, but are not limited to, a carboxyl group, a carboxymethyl (CM) group, a sulphoalkyl group (SP, SE), a methylsulfonate (S) group, a sulfated ester of cellulose, heparin, and the like, and combinations thereof. This step generally is designed to concentrate the ADAMTS13 product, put the product in a pre-formulation buffer, and further reduce non-ADAMTS13 impurities, including process-related impurities (e.g., host cell proteins, such as CHO proteins, host cell DNA, such as CHO DNA, reagents of the solvent-detergent mixture, etc), as well as product-related impurities (e.g., aggregates and non-biologically active fragments of ADAMTS13).

In one embodiment, the cation exchange resin also has one or more of the following features: large pores, perfusion flow behavior, and convective flow behavior. Non-limiting examples of commercially available cation exchange resins that may be used in the polishing step disclosed herein include POROS® S (Applied Biosystems), Convective Interaction Media (CIM®; BIA Separation), Toyopearl Gigacap S (Tosoh Bioscience, Montgomeryville, Pa.), Toyopearl Gigacap CM (Tosoh), Toyopearl SP (Tosoha), Toyopearl CM (Tosoh), MacroPrep S (Bio-rad, Hercules, Calif.), UNOsphereS (Bio-rad, Hercules, Calif.), MacroprepCM ((Bio-rad, Hercules, Calif.), Fractogel EMD SO3 (Merck), Fractogel EMD COO (Merck), Fractogel EMD SE Hicap (Merck), Cellufine Sulfate (Chisso), CM and SP Trisacryl (Pall), CM and S HyperD (Pall), Mustang S (Pall), S and CM Sepharose CL (GE Healthcare), S and CM Sepharose FF (GE Healthcare), S and CM CAPTO™ (GE Healthcare), MonoS (GE Healthcare), Source S (GE Healthcare), and the like.

Chromatography on a cation exchange resin is a well-known method in the art. In some embodiments, the cation exchange column has a maximum load of about 0.2 to about 0.5 mg ADAMTS13/mL. In a preferred embodiment, the column is loaded with at least 0.3 mg ADAMTS13/mL. Generally, during chromatography on a cation exchange resin, ADAMTS13 binds to the cation exchange resin and the buffer and certain impurities are allowed to flow through. The column to which ADAMTS13 is adsorbed then can be washed, e.g., to remove loosely-bound contaminants or impurities and/or to adjust the buffer in preparation for elution of ADAMTS13 from the cation exchange resin. ADAMTS13 then can be eluted in the eluate.

In some embodiments, the eluate obtained from the cation exchange chromatography step contains a higher amount of aggregates of ADAMTS13 than desired. In some embodiments, for example, the eluate comprises more than about 15% aggregates, which are believed to be introduced after the concentration and buffer exchange with the dialyzer step, and/or the cation exchange chromatography step.

To allow the production of ADAMTS13 with a significantly lower percentage of aggregates, certain conditions can be used with the cation exchange resin, as detailed further in FIG. 2 with respect to the cation exchange resin Poros S. For example, in some embodiments, a combination comprising purification by cation exchange chromatography followed by on-column solvent-detergent virus inactivation is used, for example as described in more detail above. This combination preferably results in lower amounts of aggregates appearing with the ADAMTS13 polypeptide in the eluate. In more preferred embodiments, the elution procedure comprises a gradient elution (rather than a step elution), which can further remove aggregates of ADAMTS13, e.g., in the descending part of the elution peak. In even more preferred embodiments, the concentration of Tween 80 in the elution buffer is greater than about 0.05%, for example about 0.06%, about 0.07%, about 0.08%, about 0.09%, preferably about 0.1%, about 0.11%, about 0.12%, about 0.13%, about 0.14%, or about 0.15%. The increased concentration is believed to have a further stabilizing effect on ADAMTS13, further preventing formation of high molecular weight structures during the elution of ADAMTS13 from the resin. By "stabilizing the ADAMTS13 protein" or "stabilizing effect on ADAMTS13" is meant tending to promote the native structure of ADAMTS13, particularly, in an intact and/or monomeric form, or a substantially intact and/or monomeric form, rather than a fragmented or aggregated form. Stabilizing may also refer to the tendency of the obtained ADAMTS13 to resist fragmentation, loss of native structure, and/or aggregation in the face of otherwise destabilizing conditions, such as varying temperatures, varying pH, ionic strengths, and the like.

The ADAMTS13 protein also may be stabilized by a matrix used during harvest, e.g., where virus inactivation by solvent-detergent treatment is performed on a concentrated harvest. Furthermore, aggregates that do form can be removed by the later purification steps, such as capture on an anion exchange chromatography column (such as ANX Sepharose, as described herein); and/or polishing by chromatography (such as tandem chromatography with Hydroxyapatite/Capto MMC, as described herein).

Using one or more modifications described above can result in an eluate comprising lower amounts of aggregates of ADAMTS13 polypeptide. For example, in preferred embodiments, the eluate from the cationic exchange column may comprise less than about 20%, less than about 18%, less than about 15%, less than about 12%, less than about 10%, or less than about 5% aggregates.

A final step of chromatography on a cation exchange resin comprises eluting the ADAMTS13 protein with an elution buffer. In some embodiments, bound ADAMTS13 is eluted from the cation exchange resin by increasing the ionic strength of the buffer. The buffer comprising ADAMTS13 used to chromatographically contact the cation exchange resin generally has a conductivity of less than about 10 mS/cm, at room temperature, e.g., less than 5 mS/cm. Further, the buffer comprising ADAMTS13 used to chromatographically contact the cation exchange resin generally has a pH of less than about 7.0, at room temperature e.g., 6.0. The elution buffer used to elute the ADAMTS13 protein from the cation exchange resin can have an ionic strength below such buffers. The resin may also be washed with a buffer having a pH equal to, or substantially equal to, the pH of the intended storage buffer.

In a preferred embodiment, the ADAMTS13 protein is eluted from the cation exchange resin with a storage buffer. Generally, by storage buffer is meant a buffer having a pH between about 5 and about 9, at room temperature and comprising calcium, a buffering compound, and a salt. The pH of the storage buffer may be greater than about 7.0 (e.g., about 7.5) at room temperature. The storage buffer may comprise less than about 10 mM $Ca^{++}$ (e.g., 2 mM $Ca^{++}$); the buffering compound may be selected from the group consisting of phosphate, tris, HEPES, histidine, imidazole, gly-gly, MES, tricine, acetate, and the like; and the salt may be selected from the group consisting of NaCl, KCl, $CaCl_2$, $MgCl_2$, and the like. In a preferred embodiment, the storage buffer has a pH of greater than 7.0 and comprises less than 10 mM calcium ions, a buffering compound, and a salt. In a more preferred embodiment, the storage buffer further comprises a non-ionic detergent, e.g., about 0.01 to about 0.5% non-ionic detergent, e.g. 0.05% non-ionic detergent. In even more preferred embodiments, the eluate is subjected to no subsequent concentration nor buffer exchange steps following elution from the cation exchange resin with the storage buffer.

In one particular embodiment, Source S (GE healthcare) is used as the cation exchange resin of the polishing step, for example, a Source S column with a bed height of about 20 cm. In such embodiments, the column may be activated with about 2 column volumes of about 2 M NaCl and equilibrated with about 6 column volumes of a buffer comprising about 20 mM MES, about 10 mM NaCl, and about 2 mM $CaCl_2$, having a pH of about 6 at room temperature. The buffer comprising ADAMTS13 may be contacted with the column at a conductivity below about 5 mS/cm at room temperature, and the column subsequently washed with the equilibration buffer, and finally the eluate comprising ADAMTS13 protein collected. After collection, the eluate may be concentrated and buffer exchanged for storage buffer, e.g., by anion exchange chromatography, diafiltration, ultrafiltration, dialysis, and the like.

In another particular embodiment, POROS S is used as the cation exchange resin in polishing the sample comprising ADAMTS13 protein. In this embodiment, the buffer comprising ADAMTS13 used to chromatographically contact the cation exchange resin may have a conductivity of less than about 5 mS/cm and a pH between about 6.1 and about 6.4. ADAMTS13 may be eluted using gradient elution, although step elution may preferably provide a more concentrated product. If gradient elution is performed, two buffers may be used, e.g., a first buffer that has a low salt content (e.g., little to no salt) and a second buffer that has a higher salt content (e.g., about 500 mM) such that the eluate pool may have a salt concentration of about 200 mM. If step elution is performed, the elution buffer may comprise a storage buffer, e.g., a storage buffer having about 300 mM NaCl, about 2 mM $CaCl_2$, about 20 mM histidine, about 0.05% Tween 80, and may have a pH of about 7.5, at room temperature. In some such embodiments, no buffer exchange is necessary after the POROS® S step, i.e., the ADAMTS13 fractions obtained from the POROS® S already are in a buffer and at a concentration suitable for storage. In still other embodiments, the ADAMTS13 fractions obtained from the POROS® S column may be subject to further concentrating and/or buffer exchange steps.

Generally, purifying recombinant ADAMTS13 protein according to some embodiments of the methods disclosed herein yields compositions of pure ADAMTS13 protein. In one embodiment, purifying recombinant protein according to the disclosed method yields ADAMTS13 protein that is at least about 90% pure, e.g., at least about 95% pure, e.g., at least about 98% pure, e.g., or at least about 99% pure. Yields of at least about 20% may be obtained according to some embodiments of the disclosed method. In one embodiment, the method provides yields of at least about 5%, e.g., about 30%, e.g., about 10%, e.g., about 20%, e.g., about 40%, e.g., about 50%, e.g., about 60%, e.g., about 70%, e.g., about 80%, e.g., about 90%, or e.g., about 95%. In some embodiments, the method provides ADAMTS13 protein having specific activity ranging from about 500 units/mg ADAMTS13 to about 1,000 units/mg ADAMTS13. In another embodiment, the method provides ADAMTS13 protein having a specific activity ranging from about 1,200 units/mg ADAMTS13 UV 280 protein to about 2,400 units/mg ADAMTS13 UV 280 protein. In another embodiment, wherein the recombinant ADAMTS13 protein is produced by CHO cells transformed with recombinant ADAMTS13 nucleic acid, purifying recombinant ADAMTS13 according to the disclosed method produces a composition that has less than about 1,000 ppm of host cell impurities. In some embodiments, the method provides at least about 2 mg/mL ADAMTS13 protein in a storage buffer.

Compositions Comprising Recombinant ADAMTS13 Protein

The present invention further provides compositions comprising recombinant ADAMTS13 purified according to a method disclosed herein. The compositions disclosed herein may be useful for storage of purified recombinant ADAMTS13. For example, in some embodiments, the purified ADAMTS13 protein is stored frozen, e.g., at less than about −60° C. The compositions disclosed herein also may be useful for therapeutic administration of the ADAMTS13 protein, and/or to prepare compositions for therapeutic administration, in particular, parenteral administration. For example, in some embodiments, the purified ADAMTS13 obtained according to methods described herein is in the form of a bulk drug substance, i.e., in a form ready for formulation into compositions for therapeutic administration.

Accordingly, another aspect of the invention relates to pharmaceutical compositions where the purified recombinant ADAMTS13 protein is mixed with excipient(s) or other pharmaceutically acceptable carriers. In preferred embodiments, the pharmaceutically acceptable carrier is pharmaceutically inert. A pharmaceutically inert carrier is one that does not react, or does not react substantially, with the active pharmaceutical, and/or in particular, does not affect, or does not substantially affect, the desired pharmaceutical properties of the active. The pharmaceutical compositions may be prepared in any manner known in the art e.g., by conventional mixing, dissolving, granulating, dragee-making, levigating, emulsifying, encapsulating, entrapping, lyophilizing, and the like.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular administration, subcutaneous administration, intramedullary administration, intrathecal administration, intraventricular administration, intravenous administration, intraperitoneal administration, intranasal administration, and the like.

Pharmaceutical compositions suitable for use in the present invention include compositions comprising ADAMTS13 as the active ingredient in an effective amount to achieve an intended purpose. An "effective amount" of ADAMTS13 as used herein can refer to that amount that augments, enhances, improves, increases, or produces a biological effect of native ADAMTS13. Biological effects of native ADAMTS13 include vWF-cleaving protease activity, based on the action of ADAMTS13 in cleaving von Willebrand factor, a large protein involved in blood clotting. An "effective amount" will include an amount of ADAMTS13 that results in decreased levels of platelet aggregation, e.g., reducing levels in an individual suffering from a blood clotting disorder to levels more comparable to an individual not suffering from the blood clotting disorder. Blood clotting disorders include, but are not limited to, thrombotic thrombocytopenic purpura (TTP) also known as Moschcowitz syndrome, Upshaw-Schulman syndrome (familial form of TTP), and stroke. An "effective amount" also includes the amount to achieve a prophylactic and/or therapeutic benefit in treating one or more blood clotting disorders and associated conditions. Determination of certain effective amounts is well within the capability of those skilled in the art.

The present invention provides methods, pharmaceutical compositions, and kits for treating and/or preventing blood clotting disorders and associated conditions in animal subjects. The term "animal subject" as used herein includes humans as well as other mammals.

The term "treating and/or preventing" as used herein includes achieving a therapeutic benefit and/or a prophylactic benefit, respectively. By therapeutic benefit is meant the reversal or amelioration of the underlying blood clotting disorder being treated. For example, in a TTP patient, therapeutic benefit includes eradicating or ameliorating one or more of the conditions and/or symptoms associated with TTP, such that an improvement is observed in the patient, notwithstanding the fact that the patient may still be afflicted with the underlying disorder. For example, treatment can provide a therapeutic benefit not only when formation of thromboses is reduced or eradicated, but also when an improvement is observed in the patient with respect to symptoms that accompany TTP, such as reduced headaches, lowered fever, and/or delayed kidney failure.

For prophylactic benefit, a pharmaceutical composition of the present invention may be administered to a patient at risk of developing a blood clotting disorder, including, for example, a patient reporting one or more of the symptoms or conditions commonly associated with blood clotting disorders like TTP, even though a diagnosis may not yet have been made.

In addition to the active ingredient, pharmaceutical compositions may comprise suitable pharmaceutically acceptable carriers such as excipients and auxiliaries that facilitate processing of the active compounds into preparations which can be used pharmaceutically.

Pharmaceutical formulations for parenteral administration generally comprise aqueous solutions of the active ingredient in water-soluble form. In some embodiments, suspensions of the active may be prepared as appropriate oily injection suspensions. Suitable lipophilic solvents or vehicles include oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase solubility of the active, e.g., to allow for the preparation of highly concentrated solutions.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

Pharmaceutical preparations for oral use can be obtained by combining the active with a solid excipient, optionally grinding a resulting mixture, and processing the mixture of granules, after adding suitable auxiliaries, if desired, to obtain tablets or dragee cores. Suitable excipients include carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof such as sodium alginate. Carriers may also be used that allow the pharmaceutical compositions to be formulated as tablets, pills, capsules, liquids, gels, syrups, slurries, solutions, suspensions, dragees, and the like, for oral and/or nasal ingestion by a patient to be treated.

Pharmaceutical preparations that can be used orally include push-fit capsules made of gelatin, as well as soft, sealed capsules made of gelatin and a coating such as glycerol or sorbitol. The push-fit capsules can contain the active mixed with fillers or binders, such as lactose or starches; lubricants, such as talc or magnesium stearate; and, optionally, stabilizers. In soft capsules, the active compounds may be dissolved or suspended in suitable liquids, such as oils, liquid paraffin, or liquid polyethylene glycol, with or without stabilizers.

Compositions comprising ADAMTS13 or other protein prepared according to a method described herein may formulated with a pharmaceutically acceptable carrier, placed in an appropriate container (or kit), and labeled for treatment of an indicated condition.

EXAMPLES

The following examples are provided for illustrative purposes and are not intended to limit the scope of the invention.

Example 1

FIG. 1 provides an exemplary method for purifying ADAMTS13 protein, according to certain embodiments of the invention as disclosed herein. In the Example provided, recombinant ADAMTS13 protein is purified from supernatant collected from culturing CHO cells comprising a recombinant ADAMTS13 nucleotide sequence. In this example, the sample is cell culture supernatant comprising about 2 units/ml (approximately 2 µg/mL) ADAMTS13 protein.

As shown in FIG. 1, a sample comprising ADAMTS13 and non-ADAMTS13 impurities may first be subject to an optional pre-enrichment preparation: (a) as shown in step 101, the sample may be concentrated by ultrafiltration (about 10-fold to about 20-fold) and the buffer exchanged by diafiltration (molecular weight cut-off of about 30 kDa); and (b) as shown in step 102, the ADAMTS13 protein can be bond to and eluted from an anion exchange resin, prior to further enrichment.

Pre-enrichment Preparation of the Sample
(a) Pre-Enrichment Ultrafiltration/Diafiltration (UF/DF)

As shown in FIG. 1, step 101, to optimize loading for pre-enrichment anion exchange chromatography, the cell culture supernatant is concentrated by about 10 fold to about 20 fold and diafiltrated using a PES membrane (about 30 kDa to about 50 kDa cutoff; Pall Omega) to a low-conductivity buffer containing calcium and zinc ions, which are considered to stabilize ADAMTS13. The buffer for the cell culture supernatant diafiltration is 20 mM Tris, 0.1% Polysorbate 80, 85 mM NaCl, 2 mM $CaCl_2$, 5 µM $ZnCl_2$, with a pH of 7.7 at room temperature.

(b) Pre-Enrichment Anion Exchange Chromatography

As shown in FIG. 1, step 102, pre-enrichment anion exchange chromatography may be performed using ANX Sepharose Fast Flow low sub from GE Healthcare. This anion exchange resin may be used according to the following conditions (Tables 1-2).

Column load: max. 0.5 mg ADAMTS13 Ag/ml resin; Bed height: 20 cm

TABLE 1

| Step | Buffer | Column Volume (CV) | Flow rate (cm/h) |
| --- | --- | --- | --- |
| Column activation | ANX-HS | 2 | 100 |
| Equilibration | ANX-Equi | 6 | 100 |
| Load | Concentrated and diafiltrated CCS | | |
| Wash 1 | ANX-W1 | 2.5 | 100 |
| Wash 2 | 12.5% ANX-EluB/ 87.5% ANXEluA | 3 | 100 |
| Elution gradient | 12.5% ANX-EluB/ 87.5% ANXEluA to 100% ANX-EluB | 11 | 100 |
| Post elution | ANX-HS | 3 | 100 |

Alternatively, step elution can be used with 2.8 column volumes of a buffer comprising 48% ANX-EluB and 52% ANX-EluA, as detailed in Table 2. Other potentially suitable buffers are indicated also.

TABLE 2

| Buffer | Formulation |
| --- | --- |
| ANX-Equi | 20 mM Tris, 0.1% Polysorbate 80, 50 mM NaCl, 2 mM $CaCl_2$, 5 µM $ZnCl_2$, pH = 7.7 (room temp.) |
| ANX-W1 | 20 mM Tris, 0.1% Polysorbate 80, 50 mM NaCl, pH = 7.7 (room temp.) |
| ANX-EluA | 20 mM Na/K $PO_4$, pH = 7.0 (room temp.) |
| ANX-EluB | 20 mM Na/K PO4, 400 mM NaCl, pH = 7.0 (room temp.) |
| ANX-HS | 2M NaCl |

Different resins may be used from that indicated in FIG. 1, step 102. For example, POROS 50D and POROS 50PI from Applied Biosystems, Foster City, Calif. can be used. The eluate from the pre-enrichment anion exchange chromatography using this resin can provide recombinant ADAMTS13 with a purity of about 20% to about 70%, and the percent yield after this pre-enrichment preparation of the sample can be at least about 75%.

Enrichment of ADAMTS13

As shown in FIG. 1, steps 103 and 104, respectively, ADAMTS13 may then be enriched via polishing steps (a) and (b). The sample comprising ADAMTS13 is subjected to tandem chromatography, first with hydroxyapatite on a Hydroxyapatite Type II column (Biorad, Hercules, Calif.), step 103, followed by mixed mode chromatography on a cation exchange/hydrophobic interaction resin CAPTO™ MMC (GE Healthcare), step 104. More specifically, the eluate pool from the pre-enrichment anion exchange chromatography of step 102 is diluted 1:4 with hydroxyapatite-dilution buffer to reduce the conductivity to about 6 mS/cm. The diluted eluate pool is subjected to tandem chromatography with hydroxyapatite under conditions that allow a substantial portion of ADAMTS13 protein to flow through, step 103, followed by a mixed mode cation exchange/hydrophobic interaction resin that binds ADAMTS13 protein, step 104. The conditions for the tandem chromatography are provided below and in Tables 3-4.

Column 1: Resin: Hydroxyapatite Type II (Biorad) (HA); load: max. 2 mg total protein/mL resin; bed height: 20-30 cm.

Column 2: Resin: Capto MMC (GE Healthcare); load: 3-6 mg ADAMTS13/ml resin; bed height: 10 cm.

Ratio Column volume HA:MMC=10:1.

TABLE 3

| Step | Buffer | Column Volume (CV) | Flow rate (cm/h) |
| --- | --- | --- | --- |
| Activation (MMC) | MMC-Elution | 3 (MMC) | 50 (MMC) |
| Equilibration | HA-Equi. | 4 (HA) | 50 (HA) |
| Equilibration | HA-Equi. | 1 (HA) | 50 (HA) |
| Load | Diluted Capture Eluate (1:5 diluted with HA-Equi) < 6 mS/cm conductivity | 20-30 L | 30 (HA) |
| Re-equilibration | HA-Equi. | 0.5 (HA) | 30 (HA) |
| Wash 1 (MMC) | MMC-Equi. | 3 (MMC) | 50 (MMC) |
| Wash 2 (MMC) | MMC-Wash | 4 (MMC) | 50 (MMC) |
| Elution (MMC) | 75% MMC elution buffer/ 25% MMC wash buffer | 4 (MMC) | 50 (MMC) |

TABLE 4

| Buffer | Formulation | Conductivity |
| --- | --- | --- |
| HA-Dilution | 20 mM Na/K PO$_4$, pH 7.0 (room temp.) | |
| TANDEM-Equi. | 20 mM Na/K PO$_4$, 25 mM NaCl, pH 7.0 (room temp.) | About 5.5 mS/cm (room temp.) |
| MMC-Wash | 50 mM Na/K PO$_4$, 160 mM NaCl, pH 8.0 (room temp.) | About 16.5 mS/cm (room temp.) |
| MMC-Elution | 50 mM Na/K PO$_4$, 1000 mM NaCl, pH 8.0 (room temp.) | About 93 mS/cm (room temp.) |
| HA-Elution | 300 mM K PO$_4$, pH 7.0 (room temp.) | About 33 mS/cm (room temp.) |

The percent yield ADAMTS13 after enrichment by tandem chromatography may be at least 60%.

Virus Inactivation

As shown in FIG. 1, step 105, the sample can be subjected to solvent-detergent treatment to inactivate contaminating viruses or viral particles; and/or the sample is filtered to remove such viruses or viral particles. Also as shown in FIG. 1, virus inactivation step 105 can be carried out at various points in the procedure, for example, before the tandem chromatography steps 103 and 104, or after a step involving concentration and buffer exchange, step 106, described below.

For virus inactivation by solvent-detergent treatment, the sample is treated with a solvent-detergent mixture comprising 1% TRITON X-100®, 0.3% Tri-N-butylphosphate, and 0.3% polysorbate 80, for 30 minutes at about 12° C. to about 16° C. (specifically to inactivate lipid-enveloped viruses). Additional details are provided below in Example 2.

Alternatively, or in addition, the sample is subjected to filtration, e.g., nanofiltration through a 0.2 μm particle filter. For example, the mixture after solvent-detergent treatment is diluted with 1 volume of a polishing equilibration buffer, described below, and filtered through a 0.2 μm PVDF or PES membrane. Filtration can be carried out before and/or after solvent-detergent treatment. Filtration after the treatment may be used to remove particulate matter that may have formed during the treatment. Filtration also can be carried out by nanofiltration using a 20 N filter (Planova, Asahi Kasei), as shown in FIG. 1, where the virus inactivation step 105 is carried out before the tandem chromatography steps 103 and 105. A further virus inactivation step 105 can be carried out after the sample has been polished by cation exchange chromatography, as described below.

The percent yield ADAMTS13 from this virus inactivation may be at least 95%.

Polishing by Cation Exchange Chromatography

Following enrichment, the ADAMTS13 may be polished by chromatography on a cation exchange resin, and the conductivity of the buffer comprising ADAMTS13 may be reduced prior to polishing, to achieve an appropriate conductivity for the cation exchange chromatography. Accordingly, post-enrichment steps may involve (a) reducing buffer conductivity; followed by (b) cation exchange chromatography.

(a) Reducing Buffer Conductivity

As shown in FIG. 1, step 106, preparation for cation exchange chromatography may involve concentration and buffer exchange, using UF/DF, with a cut-off of 10 kDa, and Dialyzer hardware. In the illustrated embodiment, the Dialyzer hardware used for buffer exchange involves a hollow-fiber hemodialysis module (Aquamax series, PES chemistry of the Hollowfibers, Edwards Lifesciences, Unterschleiheim, Germany) having 0.3-1.9 m$^2$ filter area. During operation, the following parameters are monitored on-line: pressure (before the module, after the module, and transmembrane pressure), conductivity, and temperature. The dialyzer cartridge is connected with two pumps, one feeding the sample (through the hollow fibers) and one feeding the dialysis buffer (surrounding the hollow fibers, in reverse flow direction). Approximately 2 m$^2$ of filter area is used for about 5 L of sample; and the fluid flow is fixed in the following way: 40 ml/min (sample flow or 20 ml/min/m$^2$ filter area), 60 ml/min (dialysis buffer flow, reverse flow). Before and after dialysis, the hollowfiber module is rinsed with dialysis buffer and the post-dialysis rinse added to the collected product. After dialysis, the sample has about the same volume as before, although it is slightly concentrated.

The percent yield ADAMTS13 after reducing the buffer conductivity in this way may be about 90%.

In other embodiments, buffer exchange may be carried out by anion exchange chromatography on ANX Sepharose-FF low sub, as in step 102.

Cation Exchange Chromatography

As shown in FIG. 1, step 107, after enrichment of ADAMTS13 protein (and the optional concentration and buffer exchange step 106 and/or the virus inactivation step 105), the sample may be polished by cation exchange chromatography. The buffer comprising ADAMTS13 protein is polished either on a Source S column (GE Healthcare) or a POROS® S column, such as on POROS® 50 HS column (Applied Biosystems).

The conditions for polishing on the Source 30S column are provided in Table 5 and buffers for the polishing step are provided in Table 6.

Resin: Source 30 S (GE Healthcare); Column load: max. 0.2 (0.5) mg ADAMTS13/ml resin; Bed height: 20 cm.

TABLE 5

| Step | Buffer | Column Volume (CV) | Flow rate (cm · h) |
| --- | --- | --- | --- |
| Column activation | 2M NaCl | 2 | 32 |
| Equilibration | SOS-Equi. | 6 | 32 |
| Load | | | 32 |
| Wash | SOS-Equi. | 3 | 32 |
| Elution (gradient) | 100% SOS-Equi./0% SOS-Elu. to 0% SOS-Equi./100% SOS-Elu. | 5 | 19 |
| Post elution | SOS-Elu. | 3 | 32 |

TABLE 6

| Buffer | Formulation | Comments |
| --- | --- | --- |
| SOS-Equi. | 20 mM MES, pH 6.0 (room temp.) | Buffer may contain 10 mM NaCl, 2 mM CaCl$_2$ |
| SOS-Elu. | 20 mM MES, 500 mM NaCl, 2 mM CaCl$_2$, pH 6.0 (room temp.) | |

The eluate pool from the Source S column is concentrated and diafiltrated against storage buffer.

The conditions for polishing on the POROS® S column are provided in Table 7 and buffers for the polishing step on are provided in Table 8.

Resin: POROS® S (Applied Biosystems, Foster City, Calif.); Column load: max. 12 mg ADAMTS13/ml resin; Bed height: 20 cm.

TABLE 7

| Step | Buffer | Column Volume (CV) | Flowrate (cm/h) |
|---|---|---|---|
| Column activation | 2M NaCl | 5 CV | 50 |
| Equilibration | Poros Equi. | 10 CV (until pH and conductivity give flat and stable signals) | 50 |
| Load | MMC-Eluate after solvent-detergent treatment and dilution | conductivity less that 5 mS/cm (room temp.) | 32 |
| Re-equilibration | Poros Equi. | 5 CV | 32 |
| Wash 1 | Poros Wash 1 | 5 CV | 32 |
| Wash 2 | Poros Wash 2 | 7 CV | 32 |
| Elution | Poros Elu. | 5 CV | 19 |
| Post elution | 2M NaCl | 3 CV | 32 |

TABLE 8

| | |
|---|---|
| Poros Equi. | 20 mM MES Acid, 30 mM NaCl, 0.1% Tween 80, pH 6.0 (room temp.), about 3.9 mS/cm conductivity at 25° C. |
| Poros Wash 1 | 20 mM L-Histidine, 5 mM NaCl, 2 mM CaCl$_2$, 0.05% Tween 80, pH 6.0 (room temp.), about 1.9 mS/cm conductivity at 25° C. |
| Poros Wash 2 | 20 mM L-Histidine, 5 mM NaCl, 2 mM CaCl$_2$, 0.05% Tween 80, pH 7.5 (room temp.), 1.9 mS/cm conductivity at 25° C. |
| Poros Elu. | 20 mM L-Histidine, 300 mM NaCl, 2 mM CaCl$_2$, 0.05% Tween 80, pH 7.5 (room temp.), about 18 mS/cm conductivity at 25° C. |

The eluate pool from the POROS® S column is concentrated and diafiltrated against storage buffer.

The percent yield ADAMTS13 after this further polishing step may be at least about 70%, and after the buffer exchange, at least about 90%.

As shown in FIG. 1, step 108, a purified ADAMTS13 protein is obtained in according to the method described above. The ADAMTS frozen and stored, e.g., at less than about −60° C. The yield of the entire process may be about 22% to about 24% or more.

Example 2

FIG. 2 provides a summary of various conditions that can be used with cation exchange chromatography step 107 of FIG. 1. In particular, comparison of the ADAMTS13 product obtained from the various runs indicates that the conditions of FIG. 2C reduce contaminating aggregates.

As shown in FIG. 2A, variation A is a combination of viral inactivation using solvent-detergent (S/D) treatment, as discussed in more detail below, followed by a cation exchange chromatography on Poros S applying a step elution. As shown in FIG. 2B, variation B involves cation exchange chromatography on Poros 50S, with step dilution, but without being preceded by virus inactivation. Both variations A and B can be performed according a procedure outlined in Table 9.

TABLE 9

| | Buffer volume (CV) | Buffer Composition | Flow rate (cm/h) | Observations |
|---|---|---|---|---|
| Activation | 5 | 2M NaCl | 50 | |
| Equilibration | 6 | 20 mM MES Acid, 30 mM NaCl, pH 6.0 (room temp.) | 50 | |
| Product loading | about 12 | S/D treated and diluted product solution | 32 | Column load max. 6 mg ADAMTS13/ml resin |
| Wash 1 | 10 | 20 mM MES acid, 30 mM NaCl, pH 6.0 (room temp.) | 32 | |
| Wash 2 | 8 | 20 mM Histidine, 30 mM NaCl, 2 mM CaCl$_2$, 0.05% Tween 80, pH 7.0 (room temp.) | 32 | |
| Step elution | 5 | 20 mM Histidine, 200 mM NaCl, 2 mM CaCl$_2$, 0.05% Tween 80, pH 7.5 (room temp.) | 25 | Pooling starts after the UV$_{280}$ signal rises significantly and pooling ends after the UV$_{280}$ signal drops below 5% of the UV$_{280}$ signal at the peak maximum (approximately 1 CV) |

In variation A, the conditioned (dialyzed) eluate from step 106 is subjected to a solvent-detergent virus inactivation step 105. The eluate is first filtered through a filter with 0.2μ pore size to remove particular matter. Then the filtrate is supplemented with a solvent-detergent mixture to final concentrations of 1% Triton X-100, 0.3% tri-n-butyl phosphate and 0.3% Polysorbate 80 (Tween 80) from stock solutions. The inactivation is performed at temperatures ranging from about 12° C. to about 25° C. in a time frame of about 30 minutes to about one hour under slight stirring or shaking. The inactivation is stopped by diluting the solution with one volume of cold dilution buffer (20 mM MES, pH 6.0, room temp.). To protect the column, the solvent-detergent treated and diluted solution is filtered again with a 0.2μ filter, for example, to remove particulate matter that may have formed during the virus inactivation treatment.

The solvent-detergent inactivated and diluted product solution is then subjected to cation exchange chromatography step 107 on Poros 50HS, using step dilution. Chromatographic details are outlined in Table 9 above. The resulting eluate pool provides the ADAMTS13 protein in the form of bulk drug substance, which can be stored frozen at less than −60° C.

In variation B, the cation exchange chromatography step 107 is carried out on the conditioned (dialyzed) eluate from step 106, without the solvent-detergent virus inactivation step 105. Details for the cation exchange chromatography are as detailed above.

As shown in FIG. 2C, variation C is a combination involving purification by cation exchange chromatography on Poros 50HS, using gradient elution, followed by on-column solvent-detergent virus inactivation. This variation surprisingly reduces aggregates otherwise found with purified ADAMTS13 protein. Chromatographic details that may be used with variation C are outlined in Table 10 below.

In variation C, the load material is the eluate pool of the cation exchange polishing step 104 and preferably has a conductivity below 4.5 mS/cm, achieved by dialysis or buffer exchange by gel filtration. Notably, the cation exchange chromatography on Poros S is adapted to include an on-column solvent-detergent treatment, which involves virus inactivation of virus immobilized on the chromatographic column, as discussed above. The on-column virus inactivation comprises a wash for one hour with the solvent-detergent mixture at 2° C. to 10° C. After the on-column treatment, the wash buffer is changed to efficiently wash out solvent-detergent chemicals prior to elution.

Elution is changed from step elution with 200 mM NaCl to a gradient elution, which is believed to facilitate separation of monomeric and oligomeric species of ADAMTS13, particularly in the descending part of the elution peak. Aggregates are removed in the late eluting fraction, thereby further removing aggregates otherwise found with purified ADAMTS13 protein. As a further adaptation to stabilize monomeric ADAMTS13 protein, the concentration of Tween 80 in the elution buffer is increased from 0.05% to 0.1% in the wash and elution buffers. This is believed to further prevent formation of aggregates during the elution of ADAMTS13 from the Poros S resin. The details of the chromatographic procedure on Poros S, including virus inactivation by on-column solvent-detergent treatment, are outlined in Table 10 above.

As shown in FIG. 2D, variation D serves as a control. In variation D, step 107 polishing via cation exchange chromatography is performed on Poros 50 HS again with gradient elution and increased Tween 80 in the elution buffer, but without on-column virus inactivation by solvent-detergent treatment. A virus inactivation solvent-detergent treatment step 105 is performed instead on concentrated harvest prior to cation exchange. The chromatographic details are provided in Table 11 below.

TABLE 10

|  | Buffer volume (CV) | Buffer composition | Flow rate (cm/h) | Comments |
| --- | --- | --- | --- | --- |
| Activation | 5 | 2M NaCl | 50 |  |
| Equilibration | 6 | 20 mM MES acid, 30 mM NaCl, pH 6.0 (room temp.) | 50 |  |
| Product loading | about 6 | Dialyzed eluate pool of the Capto MMC purification | 32 | Column load max. 6 mg ADAMTS13/ml resin |
| Wash 1 | 10 | 20 mM MES acid, 30 mM NaCl, pH 6.0 (room temp.) | 32 |  |
| Wash 2 | 1.5 | 20 mM MES acid, 30 mM NaCl, 1% Triton X-100, 0.3% TNBP, 03% 0.3% Tween 80, pH 6.0 (room tmep.) | 32 |  |
| Wash 3 | 2.1 | 20 mM MES acid, 30 mM NaCl, 1% Triton X-100, 0.3% TNBP, 03% 0.3% Tween 80, pH 6.0 (room temp.) | 20 | S/D Treatment: 1 hour contact time with S/D chemicals |
| Wash 4 | 10 | 20 mM MES acid, 30 mM NaCl, pH 6.0 (room temp.) | 32 | Removal of S/D chemicals |
| Wash 5 (buffer A) | 8 | 20 mM Histidine, 30 mM NaCl, 2 mM $CaCl_2$, 0.1% Tween 80, pH 7.0 (room temp.) | 32 | Conditioning column for elution |
| Step Elution | 10 | Gradient from 100% buffer A to 100% buffer B (20 mM Histidine, 300 mM NaCl, 2 mM $CaCl_2$, 0.1% Tween 80, pH 7.5 (room temp.) within 10 CV | 32 | Pooling starts after the $UV_{280}$ signal rises significantly and pooling end after the $UV_{280}$ signal drops below 5% of the $UV_{280}$ signal at the peak maximum (about 2-3 CV) |

TABLE 11

| | Buffer volume (CV) | Buffer composition | Flow rate (cm/h) | Comments |
|---|---|---|---|---|
| Activation | 5 | 2M NaCl | 50 | |
| Equilibration | 6 | 20 mM MES acid, 30 mM NaCl, pH 6.0 (room temp.) | 50 | |
| Product loading | about 6 | Dialyze eluate pool of the Capto MMC purification | 32 | Column load max. 6 mg ADAMTS13/ml resin |
| Wash 1 | 10 | 20 mM MES acid, 30 mM NaCl, pH 6.0 (room temp.) | 32 | |
| Wash 2 (buffer A) | 10 | 20 mM Histidine, 30 mM NaCl, 2 mM $CaCl_2$, 0.1% Tween 80, pH 7.0 (room temp.) | 32 | Conditioning column for elution |
| Step elution | 10 | Gradient from 100% buffer A to 100% buffer B (20 mM Histidine, 300 mM NaCl, 2 mM $CaCl_2$, 0.1% Tween 80, pH 7.5 (room temp.) within 10 CV | 32 | Pooling starts after the $UV_{280}$ signal rises significantly and pooling ends after the $UV_{280}$ signal drops below 5% of the $UV_{280}$ signal at the peak maximum (about 2-3 CV) |

In variation D, the load material is the eluate pool of the cation exchange polishing step 104 and preferably has a conductivity of below 4.5 mS/cm, achieved by dialysis or buffer exchange by gel filtration. The cation exchange chromatography step 107 on Poros S again uses gradient elution, instead of step elution, as well as 0.1% Tween 80 in the wash and elution buffers, as described above. The details of the chromatographic procedure on Poros S with gradient elution are outlined in Table 11, above.

Example 3

Experiments at lab scale, using 100 L fermenter scale, were performed with the on-column solvent-detergent virus inactivation, to determine potential impact of this procedure on the performance of cation exchange chromatography step 107. The data are presented in Table 12.

TABLE 12

| Sample | Solvent-detergent procedure | Yield Poros S* % A13 Ag | Yield Poros S* % A13 Frets Units | Specific activity Units/mg A13 Ag | CHO HCP impurity ng CHO HCP/ Unit A13 | CHO HCP impurity ng CHO HCP/ mg A13 Ag | Aggregates % multimers | Aggregates % dimers | Aggregates % monomer |
|---|---|---|---|---|---|---|---|---|---|
| 1 | Solvent-detergent treatment immediately before chromatography on Poros S (variation A) | 99 | 100 | 696 | 0.49 | 346 | 9.7 | 7.0 | 83.3 |
| 2 | no solvent/detergent treatment (variation B) | 133 | 154 | 894 | 0.58 | 519 | 1.3 | 4.6 | 94.1 |
| 3 | Solvent-detergent treatment on-column (Poros S) (variation C) | 89 | 95 | 931 | 0.60 | 561 | 1.0 | 2.3 | 96.7 |
| 4 | | 87 | 117 | 905 | 0.39 | 354 | 1.0 | 3.7 | 95.3 |
| 5 | Solvent-detergent | 65 | 93 | 764 | 0.21 | 163 | 0.8 | 1.5 | 97.7 |
| 6 | | 81 | 108 | 845 | 0.38 | 324 | 0.7 | 1.5 | 97.8 |

TABLE 12-continued

| Sample | Solvent-detergent procedure | Yield Poros S* % A13 Ag | Specific activity Units/mg | CHO HCP impurity | | Aggregates | | |
|---|---|---|---|---|---|---|---|---|
| | | % A13 Ag | Frets Units | A13 Ag Units/mg | ng CHO HCP/ Unit A13 | ng CHO HCP/ mg A13 Ag | % multimers | % dimers | % monomer |
| 7 | treatment at the concentrated harvest (variation D) | 66 | 131 | 741 | 0.31 | 231 | 0.2 | 1.1 | 98.7 |

*Yields above 100% reflects an assay problem with the chromatographic load fraction on Poros 50S.
A13 Ag: ADAMTS13 antigen
A13 Frets: ADAMTS13 Frets Units
CHO HCP: Chinese hamster ovary host cell proteins As shown in Table 12, performing virus inactivation via solvent-detergent treatment in solution, prior to cation exchange chromatography on Poros S, can result in the formation of high amounts of aggregates (Variation A of FIG. 2A and Sample 1). If the solvent-detergent treatment is omitted and the same procedure carried out, aggregate formation is significantly reduced (Variation B of FIG. 2B and sample 2).

Performing the solvent-detergent treatment on-column, that is, contacting the ADAMTS13 with the solvent-detergent mixture while it is immobilized on the surface of the resin, also can prevent the formation of aggregates. In addition, the small amounts of aggregates that do form can further be removed by gradient elution in the late eluting fraction (Variation C of FIG. 2C; samples 3 and 4).

For comparison, a standard solvent-detergent treatment in solution is carried out the purification process, followed by cation exchange chromatography on Poros S without solvent-detergent treatment neither immediately before nor on-column (Variation D of FIG. 2D, samples 5, 6, and 7). This procedure also can produce ADAMTS13 with a low content of aggregates.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. An in vitro method for purifying a therapeutic protein composition, said method comprising:
   providing a solution comprising a therapeutic protein;
   immobilizing said therapeutic protein on an anion exchange resin or cation exchange resin, wherein said immobilization step is performed in the absence of a solvent-detergent mixture; and
   subsequently incubating said immobilized therapeutic protein, with a solvent-detergent mixture at concentrations and for a time period suitable to inactivate a lipid-enveloped virus, wherein said solvent-detergent mixture comprises a non-ionic detergent and an organic solvent;
   wherein said method results in a reduction in formation of aggregates of said therapeutic protein as compared to a comparable method, wherein said comparable method comprises incubation with said solvent-detergent mixture while said therapeutic protein is not immobilized, wherein said therapeutic protein is at least one selected from ADAMTS13, Factor VIII, Factor VIIa, Factor IX, von Willebrand factor, and anti-MIF antibody.

2. The method according to claim 1, wherein said solvent-detergent mixture comprises 0.3% Tri-N-butyl phosphate, 0.3% Polysorbate 80, and 1% of a detergent composition comprising octylphenol ethoxylates of general formula:

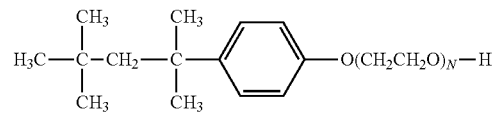

wherein the average value of N is approximately 9.5.

3. The method according to claim 1, wherein incubating with said solvent-detergent mixture is from about 30 minutes to about 1 hour.

4. The method according to claim 1, further comprising eluting said therapeutic protein from said anion exchange resin or cation exchange resin with a storage buffer.

5. The method according to claim 4, wherein said storage buffer has a pH of greater than 7.0 and comprises less than 10 mM calcium ions, a buffering compound, 0.05% non-ionic detergent, and a salt.

6. The method according to claim 4, wherein said therapeutic protein is immobilized on the cation exchange resin; and
   wherein there is an ultrafiltration, diafiltration, or buffer exchange step subsequent to the eluting step from the cation exchange resin with the storage buffer.

7. The method of claim 1, wherein said therapeutic protein is immobilized on a cation exchange resin.

8. The method of claim 1, wherein said therapeutic protein is immobilized on an anion exchange resin.

9. The method of claim 1, wherein said solvent-detergent mixture comprises at least 0.1% solvent and at least 0.1% detergent.

10. The method of claim 1, wherein said method results in a reduction of at least about 50% in the formation of aggregates of said therapeutic protein as compared to solvent-detergent treatment while said therapeutic protein is not immobilized.

11. The method of claim 1, wherein said method results in the formation of at least about 10% less aggregates of said therapeutic protein as compared to solvent-detergent treatment while said therapeutic protein is not immobilized.

* * * * *